(12) United States Patent
Shi et al.

(10) Patent No.: US 9,540,615 B2
(45) Date of Patent: *Jan. 10, 2017

(54) COMBINED CHEMICAL AND GENETIC APPROACHES FOR GENERATION OF INDUCED PLURIPOTENT STEM CELLS

(71) Applicant: The Scripps Research Institute, La Jolla, CA (US)

(72) Inventors: Yan Shi, Haidian (CN); Caroline Desponts, La Jolla, CA (US); Sheng Ding, Orinda, CA (US); Hongyan Zhou, San Francisco, CA (US); Tongxiang Lin, San Diego, CA (US); Wenlin Li, Yangpu District (CN); Saiyong Zhu, San Francisco, CA (US)

(73) Assignee: The Scripps Research Institute, La Jolla, CA (US)

(*) Notice: Subject to any disclaimer, the term of this patent is extended or adjusted under 35 U.S.C. 154(b) by 222 days.

This patent is subject to a terminal disclaimer.

(21) Appl. No.: 13/831,289

(22) Filed: Mar. 14, 2013

(65) Prior Publication Data

US 2013/0273536 A1    Oct. 17, 2013

Related U.S. Application Data

(63) Continuation of application No. 12/933,391, filed as application No. PCT/US2009/037429 on Mar. 17, 2009.

(60) Provisional application No. 61/197,986, filed on Oct. 31, 2008, provisional application No. 61/069,956, filed on Mar. 17, 2008.

(51) Int. Cl.
   *C12N 5/00*    (2006.01)
   *C12N 5/074*   (2010.01)
   *C12N 15/85*   (2006.01)

(52) U.S. Cl.
   CPC ......... *C12N 5/0696* (2013.01); *C12N 15/85* (2013.01); *C12N 2500/14* (2013.01); *C12N 2501/01* (2013.01); *C12N 2501/065* (2013.01); *C12N 2501/15* (2013.01); *C12N 2501/602* (2013.01); *C12N 2501/603* (2013.01); *C12N 2501/605* (2013.01); *C12N 2501/608* (2013.01); *C12N 2501/727* (2013.01); *C12N 2506/08* (2013.01); *C12N 2510/00* (2013.01)

(58) Field of Classification Search
   CPC .................. C12N 5/0696; C12N 15/85
   See application file for complete search history.

(56) References Cited

U.S. PATENT DOCUMENTS

| | | | |
|---|---|---|---|
| 5,824,837 A | 10/1998 | Chen et al. | |
| 5,843,780 A | 12/1998 | Thomson | |
| 6,200,806 B1 | 3/2001 | Thomson | |
| 7,029,913 B2 | 4/2006 | Thomson | |
| 7,265,138 B2 | 9/2007 | Doherty et al. | |
| 8,298,825 B1 | 10/2012 | Hochedlinger et al. | |
| 8,603,818 B1 | 12/2013 | Hochedlinger et al. | |
| 8,906,677 B2 | 12/2014 | Li et al. | |
| 9,166,832 B1 | 10/2015 | Li et al. | |
| 2002/0142457 A1 | 10/2002 | Umezawa et al. | |
| 2004/0157324 A1 | 8/2004 | Spradling et al. | |
| 2006/0182724 A1 | 8/2006 | Riordan | |
| 2007/0032447 A1 | 2/2007 | Eilertsen | |
| 2007/0128719 A1 | 6/2007 | Tseng et al. | |
| 2007/0134215 A1 | 6/2007 | Fukuda et al. | |
| 2007/0141703 A1 | 6/2007 | Stanley et al. | |
| 2007/0161107 A1 | 7/2007 | Mummery et al. | |
| 2007/0172946 A1 | 7/2007 | Smith et al. | |
| 2007/0196919 A1 | 8/2007 | Reh et al. | |
| 2007/0254359 A1 | 11/2007 | Rezania et al. | |
| 2007/0259423 A1 | 11/2007 | Odorico et al. | |
| 2007/0264709 A1 | 11/2007 | Smith et al. | |
| 2007/0269412 A1 | 11/2007 | Kopyov | |
| 2007/0281355 A1 | 12/2007 | Dalton et al. | |
| 2008/0066197 A1 | 3/2008 | Ying et al. | |
| 2008/0242594 A1 | 10/2008 | McKay et al. | |
| 2008/0268533 A1 | 10/2008 | Dalton et al. | |
| 2009/0068742 A1 | 3/2009 | Yamanaka | |
| 2009/0117439 A1 | 5/2009 | Fujinami et al. | |
| 2009/0203690 A1 | 8/2009 | Akritopoulou-Zanze et al. | |
| 2009/0227032 A1 | 9/2009 | Yamanaka et al. | |
| 2010/0233804 A1 | 9/2010 | Zhou et al. | |
| 2010/0267141 A1 | 10/2010 | Shi et al. | |
| 2011/0033931 A1 | 2/2011 | Schwartz et al. | |
| 2011/0039332 A1 | 2/2011 | Sakurada et al. | |
| 2012/0122212 A1 | 5/2012 | Grskovic et al. | |
| 2012/0129172 A1 | 5/2012 | Okano et al. | |
| 2012/0196360 A1 | 8/2012 | Okita et al. | |
| 2013/0323833 A1 | 12/2013 | Zhu et al. | |
| 2015/0079675 A1 | 3/2015 | Li et al. | |

FOREIGN PATENT DOCUMENTS

| | | |
|---|---|---|
| CN | 101356270 | 1/2009 |
| EP | 1970446 A1 | 9/2008 |
| GB | 2 437 737 | 10/2007 |

(Continued)

OTHER PUBLICATIONS

Aasen et al., Nat Biotechnol 26:1276-1284 (2008).
Beaujean et al., Dev. Biol., 2000, vol. 221, pp. 337-354.
Brons et al., Nature, 2007, vol. 448, pp. 191-195.
Chambers et al., Nature, 2007, vol. 450, pp. 1230-1234.
Chen et al., Proc Natl Acad Sci USA, 2007, vol. 104, pp. 10482-10487.
Chou et al., Cell, 2008, vol. 135, pp. 449-461.

(Continued)

*Primary Examiner* — Marcia S Noble

(74) *Attorney, Agent, or Firm* — Kilpatrick Townsend & Stockton LLP

(57) ABSTRACT

The present invention provides for identification and use of small molecules to induce pluripotency in mammalian cells as well as other methods of inducing pluripotency.

9 Claims, 5 Drawing Sheets

(56) References Cited

FOREIGN PATENT DOCUMENTS

| | | |
|---|---|---|
| GB | 2 450 603 A | 12/2008 |
| JP | 2007/508025 | 4/2007 |
| JP | 2008/307007 | 12/2008 |
| JP | 2010/529851 | 9/2010 |
| WO | 03/095628 A2 | 11/2003 |
| WO | 2009/032456 A1 | 3/2006 |
| WO | 2007/016566 A2 | 2/2007 |
| WO | 2007/069666 | 6/2007 |
| WO | 2007/113505 | 10/2007 |
| WO | 2008/015418 A2 | 2/2008 |
| WO | 2008/056173 A2 | 5/2008 |
| WO | 2008/088882 A2 | 7/2008 |
| WO | 2008/089351 | 7/2008 |
| WO | 2008/105630 A1 | 9/2008 |
| WO | 2009/006422 A1 | 1/2009 |
| WO | 2009/032194 A1 | 3/2009 |
| WO | 2009/057831 | 5/2009 |
| WO | 2009/067756 A1 | 6/2009 |
| WO | 2009/067757 A1 | 6/2009 |
| WO | 2009/073523 A2 | 6/2009 |
| WO | 2009/117439 A1 | 9/2009 |
| WO | 2010/077955 A1 | 7/2010 |
| WO | 2011/047300 A1 | 4/2011 |
| WO | 2011/109695 A1 | 9/2011 |

OTHER PUBLICATIONS

Classen et al., "ROCK inhibition enhances the recovery and growth of cryopreserved human embryonic stem cells and human induced pluripotent stem cells," Molecular Reproduction and Developments, 2009, vol. 76, No. 8, pp. 722-732.
Collas et al., Reproductive BioMedicine Online: 762-770, 2006.
D'Amour et al., Nat Biotechnol, 2005, vol. 23, pp. 1534-1541.
Debs et al., J. Biol. Chem., 1990, vol. 265, pp. 10189-10102.
Demers et al., Cloning Stem Cells, 2007, vol. 9, pp. 512-522.
Dimos et al., Science, 2008, vol. 321, pp. 1218-1221.
Djuric et al., 202, Stem Cell Research and Therapy, 2010, 1 3.
Dvorak et al., Stem Cells, 2005, vol. 23, pp. 1200-1211.
Feng et al., "Molecules That Promote or Enhance Reprogramming of Somatic Cells to Induced Pluripotent Stem Cells," Cell Stem Cell, 2009, 4, 301-12.
Guo et al., Development, 2009, vol. 136, pp. 1063-1069.
Han et al., Curr Stem Cell Res Ther. 2008, vol. 3, pp. 66-74.
Hanna et al., "Treatment of Sickle Cell Anemia Mouse Model with iPS Cells Generated from Autologous Skin," Science, Dec. 21, 2007, vol. 318, pp. 1920-1922.
Hayashi et al., Cell Stem Cell. 2008, vol. 3, pp. 391-401.
Hindie et al., "Structure and allosteric effects of low-molecular-weight activators on the protein kinase PDK1," Nat Chem Biol, Oct. 2009, vol. 5, No. 10, pp. 758-764.
Ho et al., Cancer Res., 2001, vol. 61, pp. 474-477.
Hockedlinger et al., "Nuclear reprogramming and pluripotency," Nature, Jun. 2006, vol. 441, pp. 1061-1067.
Huangfu et al., "Induction of pluripotent stem cells by defined factors is greatly improved by small-molecule compounds," Nat Biotechnol, Jul. 2008, vol. 26, No. 7, pp. 795-799.
Huangfu et al., "Induction of pluripotent stem cells from primary human fibroblasts with only Oct4 and Sox2," 2008, Nature Biotechnology, 26:11, pp. 1269-1275.
Hudecz et al., Medicinal Research Reviews, 25(6): 679-736, 2005.
Kanatsu-Shinohara et al., Cell, 2004, vol. 119, pp. 1001-1012.
Kim et al., Cell, 2009, vol. 136, pp. 411-419.
Kim et al., Cell Stem Cell, 4(6):472-476, 2009.
Krippl et al., Proc. Natl. Acad. Sci. USA, 1984, vol. 81, pp. 6988-6992.
Kubicek, et al., "Reversal of H3K9me2 by a Small-Molecule Inhibitor for the G9a Histone Methyltransferase," Molecule Cell, Feb. 2007, vol. 25, No. 3, pp. 473-481.
Li et al., "Generation of rat and human induced pluripotent stem cells by combining genetic reprogramming and chemical inhibitors," Cell Stem Cell, 2009, vol. 4, pp. 16-19.
Li et al., Differentiation, 2007, vol. 75, pp. 299-307.
Li et al., "Small molecules that modulate embryonic stem cell fate and somatic cell reprogramming," Trends Pharmacol Sci, Jan. 2010, vol. 31, No. 1, pp. 36-45.
Li et al., Stem Cells 27:2992-3000 (2009).
Lin et al., Nat Methods 6:805-808 (2009).
Lowry et al., Proc Natl Acad Sci USA, 2008, vol. 105, pp. 2883-2888.
Maherali et al., "Directly Reprogrammed Fibroblasts Show Global Epigenetic Remodeling and Widespread Tissue Contribution," Cell Stem Cell, 2007, 1, pp. 55-70.
Maherali et al., "Tgfβ Signal Inhibition Cooperates in the Induction of iPSCs and Replaces Sox2 and cMyc," Current Biology, 2009, vol. 19, pp. 1718-1723.
Meissner, et al., "Direct reprogramming of genetically unmodified fibroblasts into pluripotent stem cells," Nature Biotechnology, Oct. 2007, vol. 25, No. 10, pp. 1177-1181.
Mi et al., Mol. Ther., 2001, vol. 4, pp. 339-347.
Muller et al., "Upping the Ante: Recent Advances in Direct Reprogramming," Mol. Ther., 2009, vol. 17, pp. 947-953.
Nakagawa et al., Nat Biotechnol, 2008, vol. 26, pp. 101-106.
Okita et al., Science 322: 949-953, 2008.
Oliveri et al., Regenerative Medicine, 2(5): 795-816, Sep. 2007.
Pan et al., J. Biol. Chem., 2004, vol. 279, pp. 37013-37020.
Peerani et al., EMBO J., 2007, vol. 26, pp. 4744-4755.
Plath et al., Nature Reviews, 12: 253-265, 2011.
Plews, et al., "Activation of Pluripotency Genes in Human Fibroblast Cells by a Novel mRNA Based Approach," PLoS ONE, Dec. 2010, vol. 5, No. 12, pp. 1-10.
Roberts et al., (PD98059 Enhanced Insulin, Cytokinem and Growth Factor Activation of Xanthine Oxidoreductase in Epithelial Cells Involves STAT3 and the Glucocoticoid Receptor, Journal of Cellular Biochemistry 2007, 101: 1567-1587.
Ruhnke et al., Stem Cells, 2003, vol. 21, pp. 428-436.
Saha et al., Biophys. J., 2008, vol. 94, pp. 4123-4133.
Sato et al., Dev. Biol., 2003, vol. 260, pp. 404-413.
Schugar et al., Gene Ther, 2008, vol. 15, pp. 126-135.
Schulze et al., Methods Mol Biol, 2006, vol. 329, pp. 45-58.
Sells et al., BioTechniques, 1995, vol. 19, pp. 72-78.
Shi, et al., "A Combined Chemical and Genetic Approach for the Generation of Induced Pluripotent Stem Cells," Cell Stem Cell, Jun. 2008, vol. 2, No. 6, pp. 525-528.
Shi "Induction of Pluripotent Stem Cells from Mouse Embryonic Fibroblasts by Oct4 and Klf4 with Small-Molecule Compounds," Cell Stem Cell, 2008, vol. 3, pp. 568-574.
Shields et al., J. Biol. Chem., 1997, vol. 272, pp. 18504-18507.
Silva et al., PLoS Biology, 6(10):2237-2247, Oct. 2008.
Singh et al., Stem Cells, 2007, vol. 25, pp. 2534-2542.
Stacey et al., Mol. Cell. Biol., 1987, vol. 7, pp. 523-527.
Stadtfeld et al., Science 322: 945-949, 2008.
Sullivan et al., Reproductive BioMed. Online, 16(1): 41-50, Nov. 2008.
Sylvester et al., (Arch Surg. 136:93-99, 2004).
Tada, et al., "Nuclear reprogramming of somatic cells by in vitro hybridization with ES cells," Current Biology, 2001, vol. 11, pp. 1553-1558.
Takahashi, et al., "Induction of Pluripotent Stem Cells from Mouse Embryonic and Adult Fibroblast Cultures by Defined Factors," Cell, Aug. 2006, vol. 126, No. 4, pp. 663-676.
Takahashi et al., "Induction of Pluripotent Stem Cells from Adult Human Fobroblasts by Defined Factors"; Cell, 2007 131, pp. 861-872.
Taranger et al., "Induction of Dedifferentiation, Genomewide Transcriptional Programming, and Epigenetic Reprogramming by Extracts of Carcinoma and Embryonic Stem Cells," Molecular Biology of the Cell, 2005, vol. 16, pp. 5719-5735.
Tesar et al., Nature, 2007, vol. 448, pp. 196-199.
Tojo, et al., "The ALK-5 inhibitor A-83-01 inhibits Smad signaling and epithelia-to-mesenchymal transition by transforming growth factor-β," Cancer Sci, Nov. 2005, vol. 96, No. 11, pp. 791-800.

(56) References Cited

OTHER PUBLICATIONS

Toyooka et al., Development, 2008, vol. 135, pp. 909-918.
Ueda et al., PLoS ONE 3, e2800.
Wadia et al., Curr. Opin. Biotechnol., 2002, vol. 13, pp. 52-56.
Wering et al., "c-Myc is Dispensable for Direct Reprogramming of Mouse Fibroblasts," Cell Stem Cell, 2008, 2, 10-12.
Wernig, et al., "In vitro reprogramming of fibroblasts into a pluripotent ES-cell-like state," Nature, Jul. 2007, vol. 448, No. 7151, pp. 318-324.
Yamanaka, "Strategies and New Developments in the Generation of Patient-Specific Pluripotent Stem Cells," Cell Stem Cell, Jul. 2007, vol. 1, pp. 39-49.
Ying et al, Nature, 2008, vol. 453, pp. 519-523.
Ying et al., Cell, 2003, vol. 115, pp. 281-292.
Yu et al., Science, 2007, vol. 318, pp. 1917-1920.
Xu et al., Nature 453, 338-44 (2008).
Xu et al., Nat. Biotechnol. 2002, vol. 20, pp. 1261-1264.
Zhao et al., Cell Death and Differentiation, 2007, vol. 14, pp. 489-499.
Zheng et al., Cancer Res., 2003, vol. 63, pp. 6909-6913.
Zhou, Hongyan et al.; Generation of Induced Pluripotent Stem Cells Using Recombinant Proteins; Cell Stem Cell, 4: 381-384 (2009).
Zhu et al., "Reprogramming of human primary somatic cells by OCT4 and chemical compounds," Cell Stem Cell, Dec. 3, 2010, vol. 7, No. 6, pp. 651-655.
Artyomov et al., PLoS Comput Biol 6, e1000785 (2010).
Brambrink et al., Cell Stem Cell 2, 151-9 (2008).
Christen et al., BMC Biol 8, 5 (2010).
Ernst et al., "gp130-mediated Signal Transduction in Embryonic Stem Cells Involves Activation of Jak and Ras/Mitogen-activated Protein Kinase Pathways," J. Biol. Chem., Nov. 22, 1996, vol. 271, No. 47, pp. 30163-30143.
Graf et al., Nature 462(7273):587-594 (2009).
Han et al., Nat Cell Biol 13(1):66-71 (2011).
Hanna et al., Cell 133, 250-64.
Hanna et al., Nature 462, 595-601 (2009).
Hochedlinger et al., Development 136, 509-23 (2009).
Ieda et al., Cell 142, 375-86 (2010).
Jia et al., Nat Methods 7(3):197-199 (2010).
Kim et al., "Direct reprogramming of mouse fibroblasts to neural progenitors," Proc. Natl. Acad. Sci., USA, May 10, 2011, vol. 108, No. 9, pp. 7838-7843.
Kuzmenkin et al., FASEB J. 23, 4168-80 (2009).
Mikkelsen et al., Nature 454(7200):49-55 (2008).
Okada et al., Biochem Biophys Acta 1800, 956-63 (2010).
Okita et al., Nature 448, 313-317 (2007).
Schenke-Layland et al., Stem Cell 26, 1537-46 (2008).
Silva et al., Cell 138, 722-37 (2009).
Sridharan et al., Cell 136(2):364-377 (2009).
Stadtfeld et al., Cell Stem Cell 2, 230-40 (2008).
Stadtfeld et al., Nat Methods 7, 53-55 (2010).
Szabo et al., Nature 468(7323):521-526 (2010).
Takahashi et al., Nat Protoc 2, 3081-9 (2007).
Tighe et al., BMC 8:34 doi//:www.biomedcentral.com/1471-2121/8/34, printout pp. 1-17.
Vierbuchen et al., "Direct conversion of fibroblasts to functional neurons by defined factors," Nature, Feb. 25, 2010, vol. 463, No. 7284, pp. 1035-1042.
Warren et al., Cell Stem Cell 7(5):618-630 (2010).
Wernig et al., Nat Biotechnol 26, 916-24 (2008).
Yamanaka, S. Cell 126, 663-676 (2008).
Zhou et al., Nature 455(7213):627-632 (2008).
Feldman et al., "G9a-mediated irreversible epigenetic inactivation of Oct-3/4 during early embryogenesis," Nature Cell Biology, 2006, vol. 8(2), pp. 188-194.
Wu et al., "Cellular senescence is an important mechanism of tumor regression upon c-Myc inactivation," PNAS, 2007, vol. 104(32), pp. 13028-13033.

Aoi et al., "Generation of Pluripotent Stem Cells from Adult Mouse Liver and Stomach Cells," Sciencexpress, Feb. 2008, DOI 10.1126/science.1154884, 8 pages.
Lin et al., Nat Methods 6:805-808 (2009), Supplemental Information, 7 pages.
Noggle et al., "A Molecular Basis for Human Embryonic Stem Cell Pluripotency," Stem Cell Reviews and Reports, Jan. 2005, vol. 1(2), pp. 1550-8943; DOI: 10.1385/scr:1:2:111.
Stadtfeld et al., "Reprogramming of Pancreatic β Cells into Pluripotent Stem Cells," Curr. Biol., Jun. 2008, vol. 18(12): 890, doi: 10.1016/j.cub.2008.05.010.
Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.
Wenlin et al., "Generation of novel rat and human pluripotency stem cells by reprogramming and chemical approaches," Methods in Molecular Biology, Jan. 2010, vol. 636, pp. 293-300.
Xiong et al., "Histone deacetylase inhibitors DNA methyltransferase-3B messenger RNA stability and down-regulate de novo DNA methyltransferase activity in human endometrial cells," Cancer Res., Apr. 2005, vol. 65(7), pp. 2684-2689.
Zhou et al., "Conversion of Mouse Epiblast Stem Cells to an Earlier Pluripotency State by Small Molecules," Journal of Biological Chemistry, Sep. 2010, vol. 285(39), pp. 29676-29680; DOI: 10.1074/jbc.C110.150599.
Chen et al., "Self-renewal of embryonic stem cells by a small molecule," PNAS, 103(46):17266-17271, 2006.
Watanabe et al., "A ROCK inhibitor permits survival of dissociated human embryonic stem cells," Nature Biotechnology, 25(6):681-868, 2007.
Hakelien et al., "Transient alteration of cell fate using a nuclear and cytoplasmic extract of an insulinoma cell line," BBRC, vol. 316, pp. 834-841.
Xu et al., "Revealing a core signaling regulatory mechanism for pluripotent stem cell survival and self-renewal by small molecules," PNAS, 2010, vol. 107(8), pp. 8129-8134.
Egler et al., "Histone Deacetylase Inhibition and Blockade of the Glycolytic Pathway Synergistically Induce Glioblastoma Cell Death," Clin. Cancer Res., 2008, vol. 14(10), pp. 3132-3140.
Engel et al., "Allosteric activation of the protein kinase PDK1 with low molecular weight compounds," The EMBO Journal, 2006, vol. 25, pp. 5469-5480.
Gonzalez et al., "Generation of mouse-induced pluripotent stem cells by transient expression of a single nonviral polycistronic vector," PNAS, Jun. 2009, vol. 106(22), pp. 8918-8922.
Pesce et al., "Differential expression of the Oct-4 transcription factor during mouse germ cell differentiation," Mechanisms of Development, 1998, vol. 71, pp. 89-98.
Wang et al., "The Immunophilin FKBP12 Functions as a Common Inhibitor of the TGFβ Family Type 1 Receptors," Cell, Aug. 1996, vol. 86, pp. 435-444.
Watanabe et al., "Activation of Akt signaling is sufficient to maintain pluripotency in mouse and primate embryonic stem cells," Oncogene, 2006, vol. 25, pp. 2697-2707.
Zhao et al., "Resorcylic Acid Lactones: Naturally Occurring Potent and Selective Inhibitors of MEK," The Journal of Antibiotics, Dec. 1999, vol. 52(12), pp. 1086-1094.
Condorelli, G. et al., "Cardiomyocytes induce endothelial cells to trans-differentiate into cardiac muscle: Implications for myocardium regeneration," PNAS, vol. 98, No. 19, Sep. 11, 2001, pp. 10733-10738.
Dravida, S. et al., "The transdifferentiation potential of limbal fibroblast-like cells," Developmental Brain Research, vol. 160, No. 2, Dec. 7, 2005, pp. 239-251.
Efe, Jem E. et al., "Conversion of mouse fibroblasts into cardiomyocytes using a direct reprogramming strategy," Nature Cell Biology, vol. 13, No. 3, Mar. 1, 2011, pp. 215-222.
Kaji et al., "Virus free induction of pluripotency and subsequent excision of reprogramming factors," Nature, Apr. 2009, vol. 458(7239), pp. 771-775.

(56) References Cited

OTHER PUBLICATIONS

Kim et al., "Pluripotent stem cells induced from adult neural stem cells by reprogramming with two factors," 2008, Nature 454:646-651.
Loh et al., "Generation of induced pluripotent stem cells from human blood," Blood, May 2009, vol. 113(22), pp. 5476-5479.
Takei, Shunsuke et al., "Bone morphogenetic protein-4 promotes induction of cardiomyocytes from human embryonic stem cells in serum-based embryoid body development," AJP Heart and Circulatory Physiology, vol. 296, No. 6, Jun. 2009, pp. H1793-H1803.
Takeuchi, Jun K. et al., "Directed transdifferentiation of mouse mesoderm to heart tissue by defined factors," Nature, vol. 459, No. 7247, Jun. 4, 2009, pp. 708-711.
Extended European Search Report dated Oct. 15, 2015 for European Application No. 15177122.7, filed Mar. 17, 2009.

COMBINED CHEMICAL AND GENETIC APPROACHES FOR GENERATION OF INDUCED PLURIPOTENT STEM CELLS

CROSS-REFERENCE TO RELATED PATENT APPLICATIONS

This application is a continuation of application Ser. No. 12/933,391, filed Jan. 4, 2011, which is a U.S. National Stage entry under 35 U.S.C. §371 of PCT/US2009/037429, filed Mar. 17, 2009, which claims benefit of priority to U.S. Provisional Patent Application Nos. 61/069,956, filed Mar. 17, 2008 and 61/197,986, filed Oct. 31, 2008, each of which are incorporated by reference.

REFERENCE TO A SEQUENCE LISTING, A TABLE OR A COMPUTER PROGRAM LISTING APPENDIX SUBMITTED AS AN ASCII TEXT FILE

The Sequence Listing written in file 77103-769176_ST25.TXT, created on Feb. 11, 2015, 1,273 bytes, machine format IBM-PC, MS Windows operating system, is hereby incorporated by reference.

BACKGROUND OF THE INVENTION

Stem cells are often classified as totipotent or pluripotent. A totipotent stem cell has differentiation potential which is total: it gives rise to all the different types of cells in the body. A fertilized egg cell is an example of a totipotent stem cell. Pluripotent stem cells can give rise to any cell type in the body derived from the three main germ cell layers or an embryo itself.

Pluripotent stem cells, such as embryonic stem cells (ESCs), proliferate rapidly while maintaining pluripotency, namely, the ability to differentiate into various types of cells. Embryonic stem cells are promising donor sources for cell transplantation therapies. However, human ESCs are also associated with ethical issues regarding the use of human embryos and rejection reactions after allogenic transplantation. It may be possible to overcome these issues by generating pluripotent stem cells directly from a patient's somatic cells. That somatic cell nuclei acquire an embryonic stem-like status by fusion with ESCs suggests the existence of 'pluripotency-inducing' factors. Previous studies have recently shown that retrovirus-mediated transfection with four transcription factors (Oct-3/4, Sox2, KLF4 and c-Myc), which are highly expressed in ESCs, into mouse fibroblasts has resulted in generation of induced pluripotent stem (iPS) cells. See, Takahashi, K. & Yamanaka, S. Induction of pluripotent stem cells from mouse embryonic and adult fibroblast cultures by defined factors. *Cell* 126, 663-676 (2006); Okita, K., Ichisaka, T. & Yamanaka, S. Generation of germline-competent induced pluripotent stem cells. *Nature* 448, 313-317 (2007); Wernig, M. et al. In vitro reprogramming of fibroblasts into a pluripotent ES-cell-like state. *Nature* 448, 318-324 (2007); Maherali, N. et al. Directly reprogrammed fibroblasts show global epigenetic remodeling and widespread tissue contribution. *Cell Stem Cell* 1, 55-70 (2007); Meissner, A., Wernig, M. & Jaenisch, R. Direct reprogramming of genetically unmodified fibroblasts into pluripotent stem cells. *Nature Biotechnol.* 25, 1177-1181 (2007); Takahashi, K. et al. Induction of pluripotent stem cells from adult human fibroblasts by defined factors. Cell 131, 861-872 (2007); Yu, J. et al. Induced pluripotent stem cell lines derived from human somatic cells. *Science* 318, 1917-1920 (2007); Nakagawa, M. et al. Generation of induced pluripotent stem cells without Myc from mouse and human fibroblasts *Nature Biotechnol.* 26, 101-106 (2007); Wernig, M., Meissner, A., Cassady, J. P. & Jaenisch, R. c-Myc is dispensable for direct reprogramming of mouse fibroblasts. *Cell Stem Cell* 2, 10-12 (2008). iPS cells are similar to ESCs in morphology, proliferation, and pluripotency, judged by teratoma formation and chimaera contribution.

A recent breakthrough of using defined genetic manipulation, i.e. viral transduction of few genes highly and/or specifically expressed in mouse or human embryonic stem (ES) cells, in reprogramming both mouse and human somatic cells to induced pluripotent stem (iPS) cells has opened up tremendous opportunities to generate patient-specific stem cells for various applications (e.g. cell-based therapy or drug discovery) without the controversies associated with the conventional human ES cells, as well as to study the epigenetic reversal process. Ultimate clinical application of an iPS-cell approach would largely require methods of directed differentiation of human PS cells for generating homogenous populations of lineage-specific cell types as well as eliminating risks associated with the current iPS-cell drawbacks of genetic manipulation and low efficiency/slow kinetics. Recent studies have shown that one of the previously required four genes, cMyc, is dispensable for overexpression in generating iPS cells. See, Nakagawa, M. et al. Generation of induced pluripotent stem cells without Myc from mouse and human fibroblasts *Nature Biotechnol.* 26, 101-106 (2007); Wernig, M., Meissner, A., Cassady, J. P. & Jaenisch, R. c-Myc is dispensable for direct reprogramming of mouse fibroblasts. *Cell Stem Cell* 2, 10-12 (2008). However, the reprogramming efficiency was substantially reduced with also much slower reprogramming kinetics in the absence of cMyc.

BRIEF SUMMARY OF THE INVENTION

The present invention provides methods for screening for agents that induce reprogramming or dedifferentiation of mammalian cells into pluripotent stem cells. In some embodiments, the method comprises,
a) introducing at least one of, but not all of, an Oct polypeptide, a Klf polypeptide, a Myc polypeptide, and a Sox polypeptide into non-pluripotent cells to generate transfected cells;
b) contacting the transfected cells with a library of different agents;
c) screening the contacted cells for pluripotent stem cell characteristics; and
d) correlating the development of stem cell characteristics with a particular agent from the library, thereby identifying an agent that stimulates dedifferentiation of cells into pluripotent stem cells.

In some embodiments, step a) comprises introducing one or more expression cassettes for expression of the at least one of, but not all of, an Oct polypeptide, a Klf polypeptide, a Myc polypeptide, and a Sox polypeptide into the non-pluripotent cells.

In some embodiments, step a) comprises introducing at least one of, but not all of, an exogenous Oct polypeptide, an exogenous Klf polypeptide, an exogenous Myc polypeptide, and an exogenous Sox polypeptide into the non-pluripotent cells.

In some embodiments, the particular agent is between 50-1500 daltons.

In some embodiments, step a) comprises introducing two expression cassettes into the cells, wherein each expression cassette comprises a polynucleotide encoding a different protein, wherein the protein is selected from the group consisting of an Oct polypeptide, a Klf polypeptide, a Myc polypeptide, and a Sox polypeptide, and the remaining members of the group are not introduced into the cells.

In some embodiments, step a) comprises introducing three expression cassettes into the cells, wherein each expression cassette comprises a polynucleotide encoding a different protein, wherein the protein is selected from the group consisting of an Oct polypeptide, a Klf polypeptide, a Myc polypeptide, and a Sox polypeptide, and the remaining member of the group is not introduced into the cells.

In some embodiments, the cells are human cells. In some embodiments, the cells are non-human mammalian cells. In some embodiments, the non-pluripotent cells are progenitor cells. In some embodiments, the progenitor cells are neural progenitor cells, skin progenitor cells or hair follicle progenitor cells.

In some embodiments, the Oct polypeptide is Oct4, the Klf polypeptide is Klf 4, the Myc polypeptide is c-Myc, and the Sox polypeptide is Sox2.

The present invention also provides for methods of screening for mammalian cells with pluripotent stem cell characteristics. In some embodiments, the method comprises
a) contacting cells with a MAPK/ERK kinase (MEK) inhibitor such that growth of non-pluripotent cells is inhibited and growth of pluripotent stem cells is promoted; and
b) screening the contacted cells for pluripotent stem cell characteristics.

In some embodiments, the method comprises
contacting the cells with a library of agents prior to step a); and, following step b), selecting an agent that induces pluripotent stem cell based on the results of step b).

In some embodiments, the cells are human cells. In some embodiments, the cells are mouse, dog, cow, pig, rat and non-human primate cells.

In some embodiments, the MEK inhibitor is PD0325901.

The present invention also provides methods of producing induced pluripotent stem cells from mammalian non-pluripotent cells. In some embodiments, the method comprises,
a) introducing one or more of an Oct polypeptide, a Klf polypeptide, a Myc polypeptide, and a Sox polypeptide into the non-pluripotent cells;
b) contacting the cells with an agent that inhibits H3K9 methylation or promotes H3K9 demethylation, thereby producing induced pluripotent stem cells.

In some embodiments, step a) comprises contacting the non-pluripotent cells with one or more exogenous polypeptides selected from a Klf polypeptide, an Oct polypeptide, a Myc polypeptide, and a Sox polypeptide. In some embodiments, step a) comprises at least two (e.g., 2, 3, 4, 5, or more) cycles of:
i. contacting the non-pluripotent cells with one or more exogenous polypeptides selected from a Klf polypeptide, an Oct polypeptide, a Myc polypeptide, and a Sox polypeptide;
ii. followed by culturing the cells in the absence of the exogenous polypeptides.

In some embodiments, step a) comprises introducing one or more expression cassettes for expression of a Klf polypeptide, an Oct polypeptide, a Myc polypeptide, and a Sox polypeptide into the non-pluripotent cells.

In some embodiments, the method further comprises screening the contacted cells for pluripotent stem cell characteristics.

In some embodiments, an expression cassette for expression of an Oct polypeptide and an expression cassette for expression of a Sox polypeptide are introduced into the non-pluripotent cells.

In some embodiments, the introducing step comprises introducing into the non-pluripotent cells one or more expression cassettes for expression of a KLF polypeptide and an Oct polypeptide, wherein an expression cassette for a Myc polypeptide and/or a Sox polypeptide is not introduced into the cells.

In some embodiments, the Klf polypeptide is Klf4 and the Oct polypeptide is Oct4.

In some embodiments, the non-pluripotent cells are somatic cells.

In some embodiments, the non-pluripotent cells are fibroblast cells.

In some embodiments, neither an expression cassette for expression of a Myc polypeptide nor an expression cassette for expression of a Klf polypeptide are introduced into the non-pluripotent cells.

In some embodiments, the introducing step is performed in vivo. In some embodiments, the introducing step is performed in vitro.

In some embodiments, the method further comprises, c) selecting cells that exhibit pluripotent stem cell characteristics.

In some embodiments, the non-pluripotent cells are obtained from an animal; and the induced pluripotent stem cells are differentiated into a desired cell type.

In some embodiments, the desired cell type is introduced into the animal. In some embodiments, the animal is a human. In some embodiments, the animal is a non-human animal.

In some embodiments, the selected cells do not comprise an exogenous expression cassette for expression of Oct4.

In some embodiments, the agent inhibits H3K9 methylation. In some embodiments, the agent that inhibits H3K9 methylation is BIX01294.

In some embodiments, the cells are human cells. In some embodiments, the cells are mouse cells. In some embodiments, the non-pluripotent cells are progenitor cells. In some embodiments, the progenitor cells are neural progenitor cells.

In some embodiments, the introducing step comprises introducing
a first vector comprising a promoter operably linked to a first expression cassette, the first expression cassette comprising a polynucleotide encoding Klf4;
a second vector comprising a promoter operably linked to a second expression cassette, the second expression cassette comprising a polynucleotide encoding Sox2; and
a third vector comprising a promoter operably linked to a third expression cassette, the third expression cassette comprising a polynucleotide encoding c-Myc.

In some embodiments, the vectors are retroviral, lentiviral, adenoviral vectors, standard non-viral plasmid, or episomal expression vectors.

The present invention also comprises a mixture of mammalian cells and an agent that inhibits H3K9 methylation or promotes H3K9 demethylation, wherein the cells express at least one or more of an Oct polypeptide, a Klf polypeptide, a Sox polypeptide, and a Myc polypeptide; and/or are in contact with at least one or more of an exogenous Oct polypeptide, an exogenous Klf polypeptide, an exogenous Sox polypeptide, and an exogenous Myc polypeptide.

In some embodiments, the cells comprise a first, second and third recombinant expression cassette, the first expression cassette comprising a promoter operably linked to a polynucleotide encoding a Klf polypeptide, the second expression cassette comprising a promoter operably linked to a polynucleotide encoding a Sox polypeptide; and the third expression cassette comprising a promoter operably linked to a polynucleotide encoding a Myc polypeptide.

In some embodiments, the agent inhibits H3K9 methylation. In some embodiments, the agent that inhibits H3K9 methylation is BIX01294.

In some embodiments, the cells comprise one or more retroviral, lentiviral, adenoviral, non-viral plasmid, or episomal expression vector, the one or more retroviral, lentiviral, adenoviral, non-viral plasmid, or episomal expression vector comprising the first, second and third expression cassette.

In some embodiments, the mixture comprises a first, second and third retroviral, lentiviral, adenoviral, non-viral plasmid, or episomal expression vector, the first retroviral, lentiviral, adenoviral, non-viral plasmid, or episomal expression vector comprising the first expression cassette; the second retroviral, lentiviral, adenoviral, non-viral plasmid, or episomal expression vector comprising the second expression cassette; and the third retroviral, lentiviral, adenoviral, non-viral plasmid, or episomal expression vector comprising the third expression cassette.

In some embodiments, the cells are human cells. In some embodiments, the cells are mouse cells. In some embodiments, the cells comprise progenitor cells. In some embodiments, the progenitor cells are neural progenitor cells, skin progenitor cells or hair follicle progenitor cells.

In some embodiments, the Klf polypeptide is Klf 4, the Myc polypeptide is c-Myc, and the Sox polypeptide is Sox2.

The present invention also provides for a mammalian cell(s) that endogenously expresses at least one of a protein selected from the group consisting of an Oct polypeptide, a Klf polypeptide, a Myc polypeptide, and a Sox polypeptide, wherein: the cell does not endogenously express at least one protein of the group, wherein the protein not expressed endogenously is expressed from RNA encoded by a heterologous recombinant expression cassette present in the cell, wherein the cell expresses endogenously or heterologously each of the Oct polypeptide, the Klf polypeptide, the Myc polypeptide, and the Sox polypeptide; and expression of the protein from the heterologous expression cassette results in reprogramming or dedifferentiation of the cell from a non-pluripotent cell to a pluripotent stem cell.

In some embodiments, the Oct polypeptide is Oct 4, the Klf polypeptide is Klf 4, the Myc polypeptide is c-Myc, and the Sox polypeptide is Sox2. In some embodiments, the cell endogenously expresses a Sox polypeptide and a Myc polypeptide and heterologously expresses an Oct polypeptide and a Klf polypeptide. In some embodiments, the Oct polypeptide is Oct4, the Klf polypeptide is Klf 4, the Myc polypeptide is c-Myc, and the Sox polypeptide is Sox2.

The present invention also provides for methods of inducing Oct4 expression in a cell. In some embodiments, the method comprising, contacting the cell with an agent that inhibits H3K9 methylation or promotes H3K9 demethylation, thereby inducing Oct4 expression in the cell.

In some embodiments, the cell does not express Oct4 immediately prior to the contacting step. In some embodiments, the cells that are contacted are not pluripotent cells. In some embodiments, the cells are induced to pluripotency after the contacting step.

The present invention also provides methods for inducing non-pluripotent cells into pluripotent cells. In some embodiments, the method comprises contacting the non-pluripotent cells with one or more agents that induce pluripotency and/or introducing expression cassettes into the cells to express proteins that induce pluripotency, wherein the cells are not cultured on feeder cells and the cells are attached to a solid culture surface. In some embodiments, the method further comprises screening the contacted cells for pluripotent stem cell characteristics.

In some embodiments, the cells are attached to the solid culture surface by a molecular tether, the molecular tether selected form the group consisting of matrigel, an extracellular matrix (ECM) or ECM analog, laminin, fibronectin, and collagen.

In some embodiments, the contacting step comprises the steps of a) introducing one or more expression cassettes for expression of a Klf polypeptide, an Oct polypeptide, a Myc polypeptide, and a Sox polypeptide into the non-pluripotent cells;

b) contacting the cells with an agent that inhibits H3K9 methylation or promotes H3K9 demethylation, thereby producing induced pluripotent stem cells.

The present invention also provides methods of producing induced pluripotent stem cells from mammalian non-pluripotent cells. In some embodiments, the method comprises a) contacting the cells with at least one (e.g., one, two, three, four or more) of:

an agent that inhibits H3K9 methylation or promotes H3K9 demethylation (including but not limited to BIX);

an L-type Ca channel agonist (including but not limited to BayK);

an activator of the cAMP pathway (including but not limited to forskolin);

DNA methyltransferase (DNMT) inhibitor (including but not limited to RG108 or 5-aza-C);

nuclear receptor ligand (including but not limited to dexamethasone);

a GSK3 inhibitor (including but not limited to CHIR99021);

a MEK inhibitor, a TGFβ receptor/ALK5 inhibitor (including but not limited to SB431542, A-83-01, or 2-(3-(6-Methylpyridin-2-yl)-1H-pyrazol-4-yl)-1,5-naphthyridine), a HDAC inhibitor (including but not limited to TSA, VPA, sodium butyrate, SAHA etc); and an Erk inhibitor.

thereby producing induced pluripotent stem cells.

In some embodiments, the method further comprises screening the contacted cells for pluripotent stem cell characteristics.

In some embodiments, the method comprises a) contacting the cells with:

i. an agent that inhibits H3K9 methylation or promotes H3K9 demethylation; and ii. and agent selected from the group consisting of an L-type Ca channel agonist (including but not limited to BayK);

an activator of the cAMP pathway (including but not limited to forskolin);

DNA methyltransferase (DNMT) inhibitor (including but not limited to RG108 or 5-aza-C);

nuclear receptor ligand (including but not limited to dexamethasone);

a GSK3 inhibitor (including but not limited to CHIR99021);
a MEK inhibitor,
a TGFβ receptor/ALK5 inhibitor (including but not limited to SB431542, A-83-01, or 2-(3-(6-Methyl-pyridin-2-yl)-1H-pyrazol-4-yl)-1,5-naphthyridine),
a HDAC inhibitor (including but not limited to TSA, VPA, sodium butyrate, SAHA etc); and
an Erk inhibitor.

In some embodiments, the method further comprises b) introducing one or more expression cassettes for expression of a Klf polypeptide, an Oct polypeptide, a Myc polypeptide, and/or a Sox polypeptide into the non-pluripotent cells.

In some embodiments, Klf4 and Oct 4 are introduced into the cells (and optionally, Myc and Sox are not).

The present invention also provides mixtures of mammalian cells and at least one (e.g., one, two, three, four or more) of:
an agent that inhibits H3K9 methylation or promotes H3K9 demethylation,
an L-type Ca channel agonist;
an activator of the cAMP pathway;
DNA methyltransferase (DNMT) inhibitor;
nuclear receptor ligand;
a GSK3 inhibitor;
a MEK inhibitor,
a TGFβ receptor/ALK5 inhibitor,
a HDAC inhibitor; and
an Erk inhibitor.

In some embodiments, the mixture comprises
i. an agent that inhibits H3K9 methylation or promotes H3K9 demethylation, and
ii. an agent selected from the group consisting of
an L-type Ca channel agonist;
an activator of the cAMP pathway;
DNA methyltransferase (DNMT) inhibitor;
nuclear receptor ligand;
a GSK3 inhibitor;
a MEK inhibitor,
a TGFβ receptor/ALK5 inhibitor,
a HDAC inhibitor; and
an Erk inhibitor.

In some embodiments, the cells comprise a heterologous expression cassette for expression of an Oct polypeptide and a heterologous expression cassette for expression of a Sox polypeptide.

In some embodiments, the cells are non-pluripotent cells. In some embodiments, the cells are fibroblast cells.

In some embodiments, neither an expression cassette for expression of a Myc polypeptide nor an expression cassette for expression of a Klf polypeptide are introduced into the non-pluripotent cells.

The present invention also provides compositions comprising an agent that inhibits H3K9 methylation and an agent selected from the group consisting of
an L-type Ca channel agonist;
an activator of the cAMP pathway;
DNA methyltransferase (DNMT) inhibitor;
nuclear receptor ligand;
a GSK3 inhibitor;
a MEK inhibitor,
a TGFβ receptor/ALK5 inhibitor,
a HDAC inhibitor; and
an Erk inhibitor.

The present invention also provides kits comprising
i. an agent that inhibits H3K9 methylation or promotes H3K9 demethylation; and
ii. an agent selected from the group consisting of
an L-type Ca channel agonist;
an activator of the cAMP pathway;
DNA methyltransferase (DNMT) inhibitor;
nuclear receptor ligand;
a GSK3 inhibitor;
a MEK inhibitor,
a TGFβ receptor/ALK5 inhibitor,
a HDAC inhibitor; and
an Erk inhibitor.

In some embodiments, the kits further comprise mammalian cells.

Some embodiments of the invention are set forth in claim format directly below:

1. A method of producing induced pluripotent stem cells from mammalian non-pluripotent cells, the method comprising,
a) introducing one or more of an Oct polypeptide, a Klf polypeptide, a Myc polypeptide, and a Sox polypeptide into the non-pluripotent cells;
b) contacting the cells with an agent that inhibits H3K9 methylation or promotes H3K9 demethylation, thereby producing induced pluripotent stem cells.

2. The method of claim 1, wherein step a) comprises contacting the non-pluripotent cells with one or more exogenous polypeptides selected from a Klf polypeptide, an Oct polypeptide, a Myc polypeptide, and a Sox polypeptide.

3. The method of claim 2, wherein step a) comprises at least two cycles of:
i. contacting the non-pluripotent cells with one or more exogenous polypeptides selected from a Klf polypeptide, an Oct polypeptide, a Myc polypeptide, and a Sox polypeptide;
ii. followed by culturing the cells in the absence of the exogenous polypeptides.

4. The method of claim 1, wherein step a) comprises introducing one or more expression cassettes for expression of a Klf polypeptide, an Oct polypeptide, a Myc polypeptide, and a Sox polypeptide into the non-pluripotent cells.

5. The method of claim 1, wherein an expression cassette for expression of an Oct polypeptide and an expression cassette for expression of a Sox polypeptide are introduced into the non-pluripotent cells.

6. The method of claim 1, wherein the introducing step comprises introducing into the non-pluripotent cells one or more expression cassettes for expression of a KLF polypeptide and an Oct polypeptide, wherein an expression cassette for a Myc polypeptide and/or a Sox polypeptide is not introduced into the cells.

7. The method of any of claims 1-6, wherein the Klf polypeptide is Klf4 and the Oct polypeptide is Oct4.

8. The method of any of claims 1-7, wherein the non-pluripotent cells are somatic cells.

9. The method of any of claims 1-7, wherein the non-pluripotent cells are fibroblast cells.

10. The method of any of claims 1-7, wherein neither an expression cassette for expression of a Myc polypeptide nor an expression cassette for expression of a Klf polypeptide are introduced into the non-pluripotent cells.

11. The method of any of claims 1-10, wherein the introducing step is performed in vivo.

12. The method of any of claims 1-10, wherein the introducing step is performed in vitro.

13. The method of claim any of claims 1-12, further comprising, c) selecting cells that exhibit pluripotent stem cell characteristics.

14. The method of any of claims 1-13, wherein the non-pluripotent cells are obtained from an animal; and
the induced pluripotent stem cells are differentiated into a desired cell type.

15. The method of claim 14, wherein the desired cell type is introduced into the animal.

16. The method of claim 15, wherein the animal is a human.

17. The method of claim 15, wherein the animal is a non-human animal.

18. The method of claim 13, wherein the selected cells do not comprise an exogenous expression cassette for expression of Oct4.

19. The method of any of claims 1-8, wherein the agent inhibits H3K9 methylation.

20. The method of claim 19, wherein the agent that inhibits H3K9 methylation is BIX01294.

21. The method of any of claims 1-20, wherein the cells are human cells.

22. The method of any of claims 1-20, wherein the cells are mouse dog, cow, pig, rat and non-human primate cells.

23. The method of claim any of claims 1-22, wherein the non-pluripotent cells are progenitor cells.

24. The method of claim 23, wherein the progenitor cells are neural progenitor cells, skin progenitor cells or hair follicle progenitor cells.

25. The method of any of claim 1 or 4-24, wherein the introducing step comprises introducing
a first vector comprising a promoter operably linked to a first expression cassette, the first expression cassette comprising a polynucleotide encoding Klf4;
a second vector comprising a promoter operably linked to a second expression cassette, the second expression cassette comprising a polynucleotide encoding Sox2; and
a third vector comprising a promoter operably linked to a third expression cassette, the third expression cassette comprising a polynucleotide encoding c-Myc.

26. The method of claim any of claim 1 or 4-25, wherein the vectors are retroviral, lentiviral, adenoviral, non-viral plasmid, or episomal expression vectors.

27. A method for screening for agents that induce reprogramming or dedifferentiation of mammalian cells into pluripotent stem cells, the method comprising,
a) introducing at least one of, but not all of, an Oct polypeptide, a Klf polypeptide, a Myc polypeptide, and a Sox polypeptide into non-pluripotent cells to generate transfected cells;
b) contacting the transfected cells to a library of different agents;
c) screening the contacted cells for pluripotent stem cell characteristics; and
d) correlating the development of stem cell characteristics with a particular agent from the library, thereby identifying an agent that stimulates dedifferentiation of cells into pluripotent stem cells.

28. The method of claim 27, wherein step a) comprises introducing one or more expression cassettes for expression of the at least one of, but not all of, an Oct polypeptide, a Klf polypeptide, a Myc polypeptide, and a Sox polypeptide into the non-pluripotent cells.

29. The method of claim 27, wherein step a) comprises introducing at least one of, but not all of, an exogenous Oct polypeptide, an exogenous Klf polypeptide, an exogenous Myc polypeptide, and an exogenous Sox polypeptide into the non-pluripotent cells.

30. The method of any of claims 27-29, wherein the particular agent is between 50-1500 daltons.

31. The method of claim 27, wherein step a) comprises introducing two expression cassettes into the cells, wherein each expression cassette comprises a polynucleotide encoding a different protein, wherein the protein is selected from the group consisting of an Oct polypeptide, a Klf polypeptide, a Myc polypeptide, and a Sox polypeptide, and the remaining members of the group are not introduced into the cells.

32. The method of claim 27, wherein step a) comprises introducing three expression cassettes into the cells, wherein each expression cassette comprises a polynucleotide encoding a different protein, wherein the protein is selected from the group consisting of an Oct polypeptide, a Klf polypeptide, a Myc polypeptide, and a Sox polypeptide, and the remaining member of the group is not introduced into the cells.

33. The method of any of claims 27-32, wherein the cells are human cells.

34. The method of any of claims 27-33, wherein the cells are non-human mammalian cells.

35. The method of any of claims 27-34, wherein the non-pluripotent cells are progenitor cells.

36. The method of claim 35, wherein the progenitor cells are neural progenitor cells, skin progenitor cells or hair follicle progenitor cells.

37. The method of any of claims 27-36, wherein the Oct polypeptide is Oct4, the Klf polypeptide is Klf 4, the Myc polypeptide is c-Myc, and the Sox polypeptide is Sox2.

38. A method of screening for mammalian cells with pluripotent stem cell characteristics, the method comprising,
a) contacting cells with a MAPK/ERK kinase (MEK) inhibitor such that growth of non-pluripotent cells is inhibited and growth of pluripotent stem cells is promoted; and
b) screening the contacted cells for pluripotent stem cell characteristics.

39. The method of claim 38, comprising,
contacting the cells with a library of agents prior to step a); and, following step b), selecting an agent that induces pluripotent stem cell based on the results of step b).

40. The method of any of claims 38-39, wherein the cells are human cells.

41. The method of any of claims 38-39, wherein the cells are mouse, dog, cow, pig, rat and non-human primate cells.

42. The method of any of claims 38-41, wherein the MEK inhibitor is PD0325901.

43. A mixture of mammalian cells and an agent that inhibits H3K9 methylation or promotes H3K9 demethylation, wherein the cells:
express at least one or more of an Oct polypeptide, a Klf polypeptide, a Sox polypeptide, and a Myc polypeptide; and/or
are in contact with at least one or more of an exogenous Oct polypeptide, an exogenous Klf polypeptide, an exogenous Sox polypeptide, and an exogenous Myc polypeptide.

44. The mixture of claim 43, wherein the cells comprise a first, second and third recombinant expression cassette,
the first expression cassette comprising a promoter operably linked to a polynucleotide encoding a Klf polypeptide,
the second expression cassette comprising a promoter operably linked to a polynucleotide encoding a Sox polypeptide; and
the third expression cassette comprising a promoter operably linked to a polynucleotide encoding a Myc polypeptide.

45. The mixture of any of claims 43-44, wherein the agent inhibits H3K9 methylation.

46. The method of claim 45, wherein the agent that inhibits H3K9 methylation is BIX01294.

47. The mixture of any of claims 43-46, wherein the cells comprise one or more retroviral, lentiviral, adenoviral, non-viral plasmid, or episomal expression vector, the one or more retroviral, lentiviral, adenoviral, non-viral plasmid, or episomal expression vector comprising the first, second and third expression cassette.

48. The mixture of claim 47, comprising a first, second and third retroviral, lentiviral, adenoviral, non-viral plasmid, or episomal expression vector,
the first retroviral, lentiviral, adenoviral, non-viral plasmid, or episomal expression vector comprising the first expression cassette;
the second retroviral, lentiviral, adenoviral, non-viral plasmid, or episomal expression vector comprising the second expression cassette; and
the third retroviral, lentiviral, adenoviral, non-viral plasmid, or episomal expression vector comprising the third expression cassette.

49. The mixture of claim any of claims 43-48, wherein the cells are human cells.

50. The mixture of claim any of claims 43-48, wherein the cells are mouse dog, cow, pig, rat and non-human primate cells.

51. The mixture of any of claims 43-50, wherein the cells comprise progenitor cells.

52. The mixture of claim 51, wherein the progenitor cells are neural progenitor cells, skin progenitor cells or hair follicle progenitor cells.

53. The mixture of claim any of claims 43-52, wherein the Klf polypeptide is Klf 4, the Myc polypeptide is c-Myc, and the Sox polypeptide is Sox2.

54. A mammalian cell that endogenously expresses at least one of a protein selected from the group consisting of an Oct polypeptide, a Klf polypeptide, a Myc polypeptide, and a Sox polypeptide,
wherein:
the cell does not endogenously express at least one protein of the group, wherein the protein not expressed endogenously is expressed from RNA encoded by a heterologous recombinant expression cassette present in the cell,
the cell expresses endogenously or heterologously each of the Oct polypeptide, the Klf polypeptide, the Myc polypeptide, and the Sox polypeptide; and
expression of the protein from the heterologous expression cassette results in reprogramming or dedifferentiation of the cell from a non-pluripotent cell to a pluripotent stem cell.

55. The cell of claim 54, wherein the Oct polypeptide is Oct 4, the Klf polypeptide is Klf 4, the Myc polypeptide is c-Myc, and the Sox polypeptide is Sox2.

56. The cell of any of claims 54-55, wherein the cell endogenously expresses a Sox polypeptide and a Myc polypeptide and heterologously expresses an Oct polypeptide and a Klf polypeptide.

57. The cell of claim 56, wherein the Oct polypeptide is Oct4, the Klf polypeptide is Klf 4, the Myc polypeptide is c-Myc, and the Sox polypeptide is Sox2.

58. A method of inducing Oct4 expression in a cell, the method comprising, contacting the cell with an agent that inhibits H3K9 methylation or promotes H3K9 demethylation, thereby inducing Oct4 expression in the cell.

59. The method of claim 58, wherein the cell does not express Oct4 immediately prior to the contacting step.

60. The method of any of claims 58-59, wherein the cells that are contacted are not pluripotent cells.

61. The method of any of claims 58-59, wherein the cells are induced to pluripotency after the contacting step.

62. A method for inducing non-pluripotent cells into pluripotent cells, the method comprising,
contacting the non-pluripotent cells with one or more agents that induce pluripotency and/or introducing expression cassettes into the cells to express proteins that induce pluripotency, wherein the cells are not cultured on feeder cells and the cells are attached to a solid culture surface.

63. The method of claim 62, wherein the cells are attached to the solid culture surface by a molecular tether, the molecular tether selected form the group consisting of matrigel, an extracellular matrix (ECM) or ECM analog, laminin, fibronectin, and collagen.

64. The method of claim 62, wherein the contacting step comprises the steps of claim 1, or claims dependent on claim 1.

65. A method of producing induced pluripotent stem cells from mammalian non-pluripotent cells, the method comprising,
a) contacting the cells with at least two of:
an agent that inhibits H3K9 methylation or promotes H3K9 demethylation;
an L-type Ca channel agonist;
an activator of the cAMP pathway;
DNA methyltransferase (DNMT) inhibitor;
a nuclear receptor ligand;
a GSK3 inhibitor;
a MEK inhibitor;
a TGFβ receptor/ALK5 inhibitor;
a HDAC inhibitor; and
an erk inhibitor,
thereby producing induced pluripotent stem cells.

66. The method of claim 65, wherein the contacting step comprises
a) contacting the cells with at least two of:
i. an agent that inhibits H3K9 methylation or promotes H3K9 demethylation; and
ii. and agent selected from the group consisting of
an L-type Ca channel agonist;
an activator of the cAMP pathway;
DNA methyltransferase (DNMT) inhibitor;
a nuclear receptor ligand;
a GSK3 inhibitor;
a MEK inhibitor;
a TGFβ receptor/ALK5 inhibitor;
a HDAC inhibitor; and
an erk inhibitor.

67. The method of claim 65 or 66, further comprising
b) introducing one or more expression cassettes for expression of a Klf polypeptide, an Oct polypeptide, a Myc polypeptide, and/or a Sox polypeptide into the non-pluripotent cells.

68. The method of any of claims 65-67, wherein Klf4 and Oct 4 are introduced into the cells.

69. A mixture of mammalian cells and at least two of
an agent that inhibits H3K9 methylation or promotes H3K9 demethylation,
an L-type Ca channel agonist;
an activator of the cAMP pathway;
DNA methyltransferase (DNMT) inhibitor;
a nuclear receptor ligand;
a GSK3 inhibitor;
a MEK inhibitor;
a TGFβ receptor/ALK5 inhibitor;
a HDAC inhibitor; and
an erk inhibitor.

70. The mixture of claim 69, wherein the mixture comprises:
  i. an agent that inhibits H3K9 methylation or promotes H3K9 demethylation, and
  ii. an agent selected from the group consisting of
     an L-type Ca channel agonist;
     an activator of the cAMP pathway;
     DNA methyltransferase (DNMT) inhibitor;
     a nuclear receptor ligand;
     a GSK3 inhibitor;
     a MEK inhibitor;
     a TGFβ receptor/ALK5 inhibitor;
     a HDAC inhibitor; and
     an erk inhibitor.
71. The mixture of any of claims 69-70, wherein the cells comprise a heterologous expression cassette for expression of an Oct polypeptide and a heterologous expression cassette for expression of a Sox polypeptide
72. The mixture of any of claims 69-71, wherein the cells are non-pluripotent cells.
73. The mixture of any of claims 69-72, wherein the cells are fibroblast cells.
74. The mixture of any of claims 69-73, wherein neither an expression cassette for expression of a Myc polypeptide nor an expression cassette for expression of a Klf polypeptide are introduced into the non-pluripotent cells.
75. A composition comprising at least two of:
   an agent that inhibits H3K9 methylation;
   an L-type Ca channel agonist;
   an activator of the cAMP pathway;
   DNA methyltransferase (DNMT) inhibitor;
   a nuclear receptor ligand;
   a GSK3 inhibitor;
   a MEK inhibitor;
   a TGFβ receptor/ALK5 inhibitor;
   a HDAC inhibitor; and
   an erk inhibitor.
76. The composition of claim 75, comprising
   i. an agent that inhibits H3K9 methylation and
   ii. an agent selected from the group consisting of
      an L-type Ca channel agonist;
      an activator of the cAMP pathway;
      DNA methyltransferase (DNMT) inhibitor;
      a nuclear receptor ligand;
      a GSK3 inhibitor;
      a MEK inhibitor;
      a TGFβ receptor/ALK5 inhibitor;
      a HDAC inhibitor; and
      an erk inhibitor.
77. A kit comprising at least two of:
   an agent that inhibits H3K9 methylation;
   an L-type Ca channel agonist;
   an activator of the cAMP pathway;
   DNA methyltransferase (DNMT) inhibitor;
   a nuclear receptor ligand;
   a GSK3 inhibitor;
   a MEK inhibitor;
   a TGFβ receptor/ALK5 inhibitor;
   a HDAC inhibitor; and
   an erk inhibitor.
78. The kit of claim 77, comprising
   i. an agent that inhibits H3K9 methylation and
   ii. an agent selected from the group consisting of
      an L-type Ca channel agonist;
      an activator of the cAMP pathway;
      DNA methyltransferase (DNMT) inhibitor;
      a nuclear receptor ligand;
      a GSK3 inhibitor;
      a MEK inhibitor;
      a TGFβ receptor/ALK5 inhibitor;
      a HDAC inhibitor; and
      an erk inhibitor.
79. The kit of claim 77 or 78, further comprising mammalian cells.

Other embodiments of the invention will be clear from a reading of the entire application.

DEFINITIONS

Figure 1:
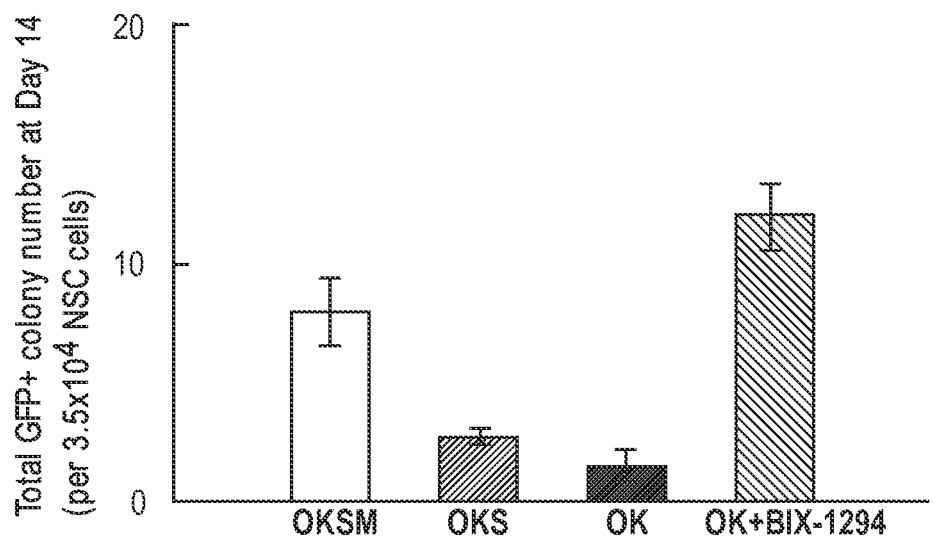
FIG. 1 Generation of iPS cells from defined primary neural progenitor cells by Oct4/Klf4 viral transduction and BIX01294 treatment. A comparison of the number of GFP+ iPS cell colonies generated from $3.5 \times 10^4$ primary OG2 neural progenitor cells by retroviral transduction of Oct4/Klf4/Sox2/c-Myc, Oct4/Klf4/Sox2, or Oct4/Klf4 with or without BIX01294 treatment.

An "Oct polypeptide" refers to any of the naturally-occurring members of Octomer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and optionally comprising a transcriptional activation domain. Exemplary Oct polypeptides include, e.g., Oct3/4 (referred to herein as "Oct4"), which contains the POU domain. See, Ryan, A. K. & Rosenfeld, M. G. *Genes Dev.* 11, 1207-1225 (1997). In some embodiments, variants have at least 90% amino acid sequence identity across their whole sequence compared to a naturally occurring Oct polypeptide family member such as to those listed above.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and optionally comprising a transcriptional activation domain. See, Dang, D. T., Pevsner, J. & Yang, V. W. *Cell Biol.* 32, 1103-1121 (2000). Exemplary Klf family members include, e.g., Klf1, Klf4, and Klf5, each of which have been shown to be able to replace each other to result in iPS cells. See, Nakagawa, et al., *Nature Biotechnology* 26:101-106 (2007). In some embodiments, variants have at least 90% amino acid sequence identity across their whole sequence compared to a naturally occurring Klf polypeptide family member such as to those listed above. To the extent a KLF polypeptide is described herein, it can be replaced with an Essrb. Thus, it is intended that for each Klf polypeptide embodiment described herein is equally described for use of Essrb in the place of a Klf4 polypeptide.

A "Myc polypeptide" refers any of the naturally-occurring members of the Myc family (see, e.g., Adhikary, S. & Eilers, M. *Nat. Rev. Mol. Cell. Biol.* 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and optionally comprising a transcriptional activation domain. Exemplary Myc polypeptides include, e.g., c-Myc, N-Myc and L-Myc. In some embodiments, variants have at least 90% amino acid sequence identity across their whole sequence compared to a naturally occurring Myc polypeptide family member such as to those listed above.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and optionally comprising a transcriptional activation domain. See, e.g., Dang, D. T., et al., *Int. J. Biochem. Cell Biol.* 32:1103-1121 (2000). Exemplary Sox polypeptides Include, e.g., Sox1, Sox2, Sox3, Sox15, or Sox18, each of which have been shown to be able to replace each other to result in iPS cells. See, Nakagawa, et al., *Nature Biotechnology* 26:101-106 (2007). In some embodiments, variants have at least 90% amino acid sequence identity across their whole sequence compared to a naturally occurring Sox polypeptide family member such as to those listed above.

"H3K9" refers to histone H3 lysine 9. H3K9 can be di-methylated at K9. See, e.g., Kubicek, et al., *Mol. Cell* 473-481 (2007).

The term "pluripotent" or "pluripotency" refers to cells with the ability to give rise to progeny that can undergo differentiation, under the appropriate conditions, into cell types that collectively demonstrate characteristics associated with cell lineages from all of the three germinal layers (endoderm, mesoderm, and ectoderm). Pluripotent stem cells can contribute to many or all tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

The term "library" is used according to its common usage in the art, to denote a collection of molecules, optionally organized and/or cataloged in such a way that individual members can be identified. Libraries can include, but are not limited to, combinatorial chemical libraries, natural products libraries, and peptide libraries.

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

"Expression cassette" refers to a polynucleotide comprising a promoter or other regulatory sequence operably linked to a sequence encoding a protein.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

The terms "agent" or "test compound" refer to any compound useful in the screening assays described herein. An agent can be, for example, an organic compound (e.g., a small molecule such as a drug), a polypeptide (e.g., a peptide or an antibody), a nucleic acid (e.g., DNA, RNA, double-stranded, single-stranded, an oligonucleotide, antisense RNA, small inhibitory RNA, micro RNA, a ribozyme, etc.), an oligosaccharide, a lipid. Usually, the agents used in the present screening methods have a molecular weight of less than 10,000 daltons, for example, less than 8000, 6000, 4000, 2000 daltons, e.g., between 50-1500, 500-1500, 200-2000, 500-5000 daltons. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., ability to induce pluripotency under certain conditions such as are described herein, creating variants of the lead compound, and evaluating the property and activity of those variant compounds. Often, high throughput screening (HTS) methods are employed for such an analysis.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Inhibitors," "activators," and "modulators" of expression or of activity are used to refer to inhibitory, activating, or modulating molecules, respectively, identified using in vitro and in vivo assays for expression or activity of a described target protein (or encoding polynucleotide), e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

DETAILED DESCRIPTION OF THE INVENTION

I. Introduction

The present invention is based, in part, on the surprising discovery that small molecules may be used to mimic the effects of the transcription factors involved in triggering induced pluripotent stem cells (iPS). For example, as described in detail herein, Oct4 can be "replaced" with a small molecule that reduced methylation of the histone 3 lysine 9 (H3K9). Thus, for example, BIX01294, a small molecule that specifically inhibits G9a (a histone methyltransferase for H3K9), when contacted to a mammalian cell in which Klf4, c-Myc and Sox2 has been expressed, results in induction of pluripotent stem cells.

These results are not only interesting with regard to the role of methylation of H3K9 and its involvement in cell programming, but also shows small molecules can be identified that replace transcription factors previously shown to be essential for induction of pluripotent stem cells. This can be of particular interest where the goal is introduction (or re-introduction) of induced pluripotent stem cells, or subsequently differentiated cells, such a progenitor cells derived from the iPS cells, into a patient. As several (e.g., Oct4, Myc) of the four iPS transcription factors have known oncogenic activities, it may be beneficial to replace these factors with other less or non-oncogenic molecules. Further, replacement of some or each of the four factors with small molecules that do not require transformation (and thus the potential oncogenic effects of DNA insertion into the chromosome) will further help to reduce the possible cancer side effects of therapies involving iPS.

The present invention also provides induced pluripotent cells in which at least some of the iPS transcription factors are expressed at endogenous or lower levels and nevertheless are pluripotent. This invention is based, in part, on the discovery that certain cells that endogenously express Sox2 can be induced to pluripotency by introduction and heterologous expression of only Oct4 and Klf4.

Further, as shown herein, non-pluripotent cells that do not endogenously or heterologously express a Sox polypeptide (e.g., Sox2) can be induced to pluripotency using the methods of the invention. For example, pluripotency can be induced by introduction of only Oct4 and Klf4 into non-pluripotent cells (e.g., fibroblast cells) that are also contacted with an agent that inhibit H3K9 methylation, and optionally also contacted with at least one of an L-type calcium channel agonist, an activator of the cAMP pathway, a DNA methyltransferase (DNMT) inhibitor, a nuclear receptor agonist, a GSK3 inhibitor, or a MEK inhibitor. The inventors have also found that combinations of agents such as a GSK inhibitor and a HDAC inhibitor; or a GSK inhibitor and a cAMP pathway activator; or a GSK inhibitor and an ALK5 inhibitor (with and without a G9a inhibitor) are effective in inducing pluripotency in cells heterologously expressing Oct4 alone, or Oct4/Sox2 or Sox2/Klf4. Accordingly, the invention provides for mixtures of cells and agents, wherein the cells are initially not pluripotent cells (e.g., are non-stem cells) and optionally heterologously or endogenously express or are otherwise in intact with Oct4 and/or Klf4, and wherein the agent(s) is one or more of an agent that inhibit H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; and/or an Erk inhibitor.

As discussed further below, the invention also provides novel methods of screening for cells with pluripotent stem cell characteristics by culturing cells to be screened with a MEK inhibitor, an agent that inhibits H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor. MEK inhibitors, for example, inhibit growth of non-iPS cells while simultaneously promoting growth and stable reprogramming of iPS cells, thereby enriching a particular cell mixture for cells with pluripotent stem cell characteristics.

II. Induction of Pluripotent Stem Cells

A. Heterologous/Endogenous Expression

In some embodiments of the invention, non-pluripotent cells are identified that endogenously express at least one (and optionally, two or three of) proteins from the group consisting of a Oct polypeptide, a Klf polypeptide, a Myc polypeptide, and a Sox polypeptide. The remaining (non-endogenously expressed) proteins from the group can then be heterologously expressed in the cells, and screened for re-programming and/or dedifferentiation into pluripotent cells, optionally in the presence of one or more of a MEK inhibitor, an agent that inhibits H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; and/or an Erk inhibitor.

It is believed that any type of mammalian non-pluripotent cell can be screened for protein expression and subsequently be converted to a pluripotent cell. In some embodiments, the starting cells are isolated progenitor cells. Exemplary progenitor cells include, but are not limited to, endoderm progenitor cells, mesoderm progenitor cells (e.g., muscle progenitor cells, bone progenitor cells, blood progenitor cells), and ectoderm progenitor cells (e.g., epidermal tissue progenitor cells and neural progenitor cells). Cells useful for these aspects of the invention can be readily identified by screening cell lines for expression of a Oct polypeptide, a Klf polypeptide, a Myc polypeptide, and a Sox polypeptide or by identifying cells with reduced promoter methylation (e.g., by DNA bisulfate sequencing) or identifying cells with a modified histone state to determine the reduced silencing state of these genes. Those transcription factors that are not expressed endogenously can then be expressed heterologously to induce pluripotency without heterologous expression of those factors already expressed endogenously.

As shown in the Examples, some cells (e.g., neural progenitor cells and fibroblasts (data not shown)) can be induced into pluripotency by heterologous expression of Oct4 and Klf4 only. This demonstrates that Sox and Myc proteins, and likely Oct and Klf proteins, need not all be overexpressed (e.g., using a high expression viral vector) to achieve pluripotency. Instead, some of these proteins can be expressed at endogenous or even lower detectable levels and still be eligible for conversion to pluripotent cells by heterologous expression of other members of the group. Thus, in some embodiments of the invention, cells are identified that endogenously express a Sox polypeptide and/or a Myc polypeptide, and an Oct polypeptide and a Klf polypeptide is heterologously expressed in the cell, thereby inducing conversion of the cell into a pluripotent cell. In some embodiments, cells are identified that endogenously express an Oct polypeptide and/or a Klf polypeptide and/or a Myc polypeptide, and a Sox polypeptide is heterologously expressed in the cell, thereby inducing conversion of the cell into a pluripotent cell. Optionally, Sall4 (Zhang et al., *Nat Cell Biol.* 8(10):1114-23 (2006)) can be expressed in pace of any or all of Myc, Klf4, and Sox2.

Efficiency of induction to pluripotency as described herein can be further improved by inclusion in non-pluripotent cells of, e.g., one or more of, UTF1, SV40, TERT (either by introduction of an expression cassette encoding these gene products, or by contacting the cells with the proteins themselves) and/or by reducing expression of p53 (e.g., by siRNA). See, e.g., Zhao, et al., *Cell Stem Cell* 3:475-479 (2008).

B. Transcription Factor Proteins

As detailed herein, a number of embodiments of the invention involves introduction of one or more polypeptides into cells, thereby inducing pluripotency in the cell. As discussed above, introduction of a polypeptide into a cell can comprise introduction of a polynucleotide comprising one or more expression cassettes into a cell and inducing expression, thereby introducing the polypeptides into the cell by transcription and translation from the expression cassette. Alternatively, one can introduce an exogenous polypeptide (i.e., a protein provided from outside the cell and/or that is not produced by the cell) into the cell by a number of different methods that do not involve introduction of a polynucleotide encoding the polypeptide.

Accordingly, for any embodiment of the invention described herein referring either to introduction of a polypeptide into a cell, or introduction of an expression cassette encoding a polypeptide into a cell, it should be understood that the present invention also expressly provides for exogenous introduction of the polypeptide as a protein into the cell. Therefore, in some embodiments, mammalian non-pluripotent cells are induced to pluripotency by a) exogenously introducing one or more of a Klf polypeptide, an Oct polypeptide, a Myc polypeptide, and/or a Sox polypeptide into the non-pluripotent cells; and optionally b) contacting the cells with one or more of a MEK inhibitor, an agent that inhibits H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor, thereby producing induced pluripotent stem cells.

In some embodiments, in some embodiments of the invention, non-pluripotent cells are identified that endogenously express at least one (and optionally, two or three of) proteins from the group consisting of a Oct polypeptide, a Klf polypeptide, a Myc polypeptide, and a Sox polypeptide. The remaining (non-endogenously expressed) proteins from the group can then be exogenously introduced in the cells, and screened for re-programming and/or dedifferentiation into pluripotent cells, optionally in the presence of one or more of a MEK inhibitor, an agent that inhibits H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor.

In some embodiments, cells are identified that endogenously express a Sox polypeptide and/or a Myc polypeptide, and as a second step an Oct polypeptide and a Klf polypeptide is exogenously introduced in the cell, thereby inducing conversion of the cell into a pluripotent cell. In some embodiments, cells are identified that endogenously express an Oct polypeptide and/or a Klf polypeptide and/or a Myc polypeptide, and a Sox polypeptide is exogenously introduced in the cell, thereby inducing conversion of the cell into a pluripotent cell.

Exogenous introduction of a polypeptide into a cell can occur in any number of ways. One or more proteins can simply be cultured in the presence of target cells under conditions to allow for introduction of the proteins into the cell. In some embodiments, the exogenous proteins comprise the transcription factor polypeptide of interest linked (e.g., linked as a fusion protein or otherwise covalently or non-covalently linked) to a polypeptide that enhances the ability of the transcription factor to enter the cell (and optionally the cell nucleus).

Examples of polypeptide sequences that enhance transport across membranes include, but are not limited to, the *Drosophila* homeoprotein antennapedia transcription protein (AntHD) (Joliot et al., New Biol. 3: 1121-34, 1991; Joliot et al., Proc. Natl. Acad. Sci. USA, 88: 1864-8, 1991; Le Roux et al., Proc. Natl. Acad. Sci. USA, 90: 9120-4, 1993), the herpes simplex virus structural protein VP22 (Elliott and O'Hare, Cell 88: 223-33, 1997); the HIV-1 transcriptional activator TAT protein (Green and Loewenstein, Cell 55: 1179-1188, 1988; Frankel and Pabo, Cell 55: 1 289-1193, 1988); delivery enhancing transporters such as described in U.S. Pat. No. 6,730,293 (including but not limited to an peptide sequence comprising at least 7-25 contiguous arginines); and commercially available Penetratin™ 1 peptide, and the Diatos Peptide Vectors ("DPVs") of the Vectocell® platform available from Daitos S. A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes.

In some embodiments, the transcription factor polypeptides described herein are exogenously introduced as part of a liposome, or lipid cocktail such as commercially available Fugene6 and Lipofectamine). In another alternative, the transcription factor proteins can be microinjected or otherwise directly introduced into the target cell.

As discussed in the Examples, the inventors have found that incubation of cells with the transcription factor polypeptides of the invention for extended periods is toxic to the cells. Therefore, the present invention provides for intermittent incubation of non-pluripotent mammalian cells with one or more of Klf polypeptide, an Oct polypeptide, a Myc polypeptide, and/or a Sox polypeptide, with intervening periods of incubation of the cells in the absence of the one or more polypeptides. In some embodiments, the cycle of incubation with and without the polypeptides can be repeated for 2, 3, 4, 5, 6, or more times and is performed for sufficient lengths of time (i.e., the incubations with and without proteins) to achieve the development of pluripotent cells. Various agents (e.g., MEK inhibitor and/or GSK inhibitor and/or TGFbeta inhibitor) can be included to improve efficiency of the method.

C. Small Molecule Replacement of iPS Transcription Factors

In some embodiments of the invention, a cell expresses (endogenously or heterologously) at least one protein selected from an Oct polypeptide, a Klf polypeptide, a Myc polypeptide, and a Sox polypeptide (e.g., at least 1, 2, or 3 of these) and is contacted with at least one agent, wherein the agent is sufficient to result in induction of the cell into a pluripotent stem cell in the absence of expression of one or more of the remaining non-expressed proteins, i.e., any of the Oct polypeptide, the Klf polypeptide, the Myc polypeptide, or the Sox polypeptide not expressed in the cell.

As shown in the Examples, contacting the cell with certain agents can "complement" or replace what is generally otherwise understood as a necessary expression of one of these proteins to result in pluripotent cells. By contacting a cell with an agent that functionally replaces expression of one of the proteins listed above, it is possible to generate pluripotent cells with expression of all of the above-listed proteins except the protein replaced or complemented by the agent. The remaining proteins can be expressed endogenously, heterologously, or in some combination of the two (for example, a Sox and Myc polypeptide could be expressed endogenously, a Klf polypeptide could be expressed heterologously and the Oct polypeptide could be "replaced" by instead contacting the cell with a complementary agent such as an agent that inhibits methylation of H3K9 or promotes H3K9 demethylation).

Further, small molecules can improve the efficiency of a process for generating pluripotent cells (e.g., iPS cells). For example, improved efficiency can be manifested by speeding the time to generate such pluripotent cells (e.g., by shortening the time to development of pluripotent cells by at least a day compared to a similar or same process without the small molecule). Alternatively, or in combination, a small molecule can increase the number of pluripotent cells generated by a particular process (e.g., increasing the number in a given time period by at least 10%, 50%, 100%, 200%, 500%, etc. compared to a similar or same process without the small molecule.

As described in the Examples, cells that heterologously express Klf4, Sox2, and Myc can be induced to pluripotency by further contacting the cells with an agent that inhibits H3K9 methylation without heterologous expression of Oct4. Indeed, it has been found that pluripotency can be induced by contacting non-pluripotent cells with an agent that inhibits H3K9 methylation and introduction of either Oct 4 alone (e.g., without also introducing a vector for expressing a Myc polypeptide, a Sox polypeptide, or a KLf polypeptide) or Oct4 with Klf4. Cells that can be induced to pluripotency include, but are not limited to, neural progenitor cells and fibroblasts. Agents that inhibit H3K9 methylation include agents that inhibit methylases (also known as methyl transferases) that target H3K9. For example, G9a histone methyltransferase methylates H3K9 and inhibition of G9a histone methyltransferase is known to reduce methylation of H3K9. See, e.g., Kubicek, et al., *Mol. Cell.* 473-481 (2007). An example of a G9a histone methyltransferase useful according to the methods of the invention is BIX01294 (see, e.g., Kubicek, et al., *Mol. Cell* 473-481 (2007)), or salts, hydrates, isoforms, racemates, solvates and prodrug forms thereof. Bix01294 is displayed below:

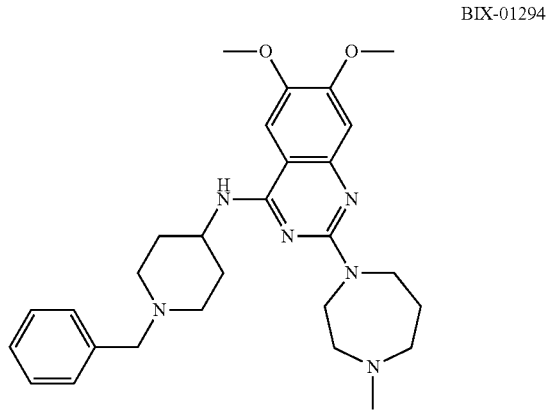 [SMILES: COc1cc2nc(N3CCCN(C)CC3)nc(NC3CCN(Cc4ccccc4)CC3)c2cc1OC]

BIX-01294

The Bix01294 compounds of the present invention also include the salts, hydrates, solvates and prodrug forms. Bix01294 possesses asymmetric carbon atoms (optical centers) or double bonds; the racemates, diastereomers, geometric isomers and individual isomers are all intended to be encompassed within the scope of the present invention. For example, the compound of the present invention can be the R-isomer or the S-isomer, or a mixture thereof. In addition, the compound of the present invention can be the E-isomer or the Z-isomer, or a combination thereof.

In some embodiments, the agent that inhibits H3K9 methylation is a substrate analog of a histone methyl transferase. The substrate of a number of methyl transferases is S-adenosyl-methionine (SAM). Thus, in some embodiments, the agent that inhibits H3K9 methylation is a SAM analog. Exemplary SAM analogs include, but are not limited to, methylthio-adenosine (MTA), sinefungin, and S-adenosyl-homocysteine (SAH). In other embodiments, the agent that inhibits H3K9 methylation does not compete with SAM on a histone methyl transferase.

The resulting pluripotent cells (from heterologous expression and/or small molecule "replacement") can develop into many or all of the three major tissue types: endoderm (e.g., interior gut lining), mesoderm (e.g., muscle, bone, blood), and ectoderm (e.g., epidermal tissues and nervous system), but, optionally, may show restrictions to their developmental potential (e.g., they may not form placental tissue, or other cell types of a defined lineage). The cells can be human or non-human (e.g., primate, rat, mouse, rabbit, bovine, dog, cat, pig, etc.).

In other embodiments, BIX01294, or other agents that inhibit H3K9 methylation or promote H3K9 demethylation can be used to induce pluripotency in cells that were previously not pluripotent. In some embodiments, an agent that inhibits H3K9 methylation is used to induce Oct4 expression in cells, or at least alterations in Oct4 promoter DNA methylation and/or histone methylation to allow for induction of cells into pluripotency. Thus, in some embodiments, cells that are not initially pluripotent cells are contacted with an agent that inhibits H3K9 methylation to induce the cells to become pluripotent. Indeed, without intending to limit the scope of the invention to a particular mode of action, the inventors believe that contacting non-pluripotent cells with an agent that inhibits H3K9 methylation or promotes H3K9 demethylation will improve any method of inducing cells to pluripotency. For example, the agent that inhibits H3K9 methylation can be contacted to a non-pluripotent cell and induced to pluripotency in a method comprising contacting the non-pluripotent cells with an agent that inhibits H3K9 methylation, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor, wherein each compound is included in an amount sufficient in improve the efficiency of induction. In some embodiments as described in this paragraph, Oct4 only, or Oct4/Klf4, or Sox2/Klf4 are further heterologously expressed in the non-pluripotent cells resulting in induction of pluripotency following contacting with agents as described herein.

The inventors have also found that the combination of a GSK inhibitor and an HDAC inhibitor, or a GSK inhibitor and a cAMP pathway activator, or a GSK inhibitor and an ALK5 inhibitor can induce to pluripotency any of mouse or human fibroblasts or keratinocytes that express any of: Oct4 alone, Oct4/Klf4 or Sox2/Klf4 (data not shown). In other embodiments, a non-pluripotent cell is induced to pluripotency in a method comprising contacting the non-pluripotent cells with a GSK3 inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor, wherein each compound is included in an amount sufficient in improve the efficiency of induction. In other embodiments, a non-pluripotent cell is induced to pluripotency in a method comprising contacting the non-pluripotent cells with a TGFβ receptor/ALK5 inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a HDAC inhibitor; or an Erk inhibitor, wherein each compound is included in an amount sufficient in improve the efficiency of induction. In other embodiments, a non-pluripotent cell is induced to pluripotency in a method comprising contacting the non-pluripotent cells with a HDAC inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, or an Erk inhibitor, wherein each compound is included in an amount sufficient in improve the efficiency of induction. In other embodiments, a non-pluripotent cell is induced to pluripotency in a method comprising contacting the non-pluripotent cells with a MEK inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a TGFβ receptor/ALK5 inhibitor, a HDAC inhibitor; or an Erk inhibitor, wherein each compound is included in an amount sufficient in improve the efficiency of induction. In other embodiments, a non-pluripotent cell is induced to pluripotency in a method comprising contacting the non-pluripotent cells with two, three, four, five, six, seven, eight, nine, or each of a MEK inhibitor, an L-type Ca channel agonist; an agent that inhibits H3K9 methylation, an activator of the cAMP pathway; a DNA methyltransferase (DNMT) inhibitor; a nuclear receptor ligand; a GSK3 inhibitor; a TGFβ receptor/ALK5 inhibitor, a HDAC inhibitor; or an Erk inhibitor, wherein each compound is included in an amount sufficient in improve the efficiency of induction. In some embodiments as described in this paragraph, Oct4 only, or Oct4/Klf4, or Sox2/Klf4 are further heterologously expressed in the non-pluripotent cells resulting in induction of pluripotency following contacting with agents as described herein.

Exemplary L-type calcium channel agonists include, but are not limited to, BayK8644 (see, e.g., Schramm, et al., *Nature* 303:535-537 (1983)), Dehydrodidemnin B (see, e.g., U.S. Pat. No. 6,030,943), FPL 64176 (FPL) (see, e.g., Liwang, et al., *Neuropharmacology* 45:281-292 (2003)), S(+)-PN 202-791 (see, e.g., Kennedy, et al., *Neuroscience* 49:937-44 (1992)) and CGP 48506 (see, e.g., Chahine, et al., *Canadian Journal of Physiology and Pharmacology* 81:135-141 (2003)).

Exemplary activators of the cAMP pathway include, but are not limited to, forskolin (see, e.g., Liang, et al., *Endocrinology* 146: 4437-4444 (2005)), FSH (see, Liang, supra), milrinone (see, Liang, supra), cilostamide (see, Liang, supra), rolipram (see, Liang, supra), dbcAMP (see, Liang, supra) and 8-Br-cAMP (see, Liang, supra).

Exemplary DNA methyltransferase (DNMT) inhibitors can include antibodies that bind, dominant negative variants of, and siRNA and antisense nucleic acids that suppress expression of DNMT. DNMT inhibitors include, but are not limited to, RG108 (available, e.g., from Sigma-Aldrich), 5-aza-C (5-azacitidine or azacitidine) (see, e.g., Schermelleh, et al., *Nature Methods* 2:751-6 (2005)), 5-aza-2'-deoxycytidine (5-aza-CdR) (see, e.g., Zhu, *Clinical Medicinal Chemistry* 3(3):187-199 (2003)), decitabine (see, e.g., Gore, *Nature Clinical Practice Oncology* 2:S30-S35 (2005)), doxorubicin (see, e.g., Levenson, *Molecular Pharmacology* 71:635-637 (2007)), EGCG ((−)-epigallocatechin-3-gallate) (see, e.g., Fang, et al., *Cancer Research* 63:7563-7570 (2003)), RG108 (see, e.g., Carninci, et al., WO2008/126932, incorporated herein by reference) and zebularine (see, Carninci, supra).

Exemplary nuclear receptor ligands, i.e., agonists, antagonists, activators and/or repressors of nuclear receptors, can modulate local gene expression or transcription at the site of delivery. Nuclear receptor agonist (and also nuclear receptor antagonists) can be used. In some embodiments, nuclear receptors are co-regulators of transcription. Activation or inhibition of certain nuclear receptors regulate epigenetic states of specific gene loci where they bind. The inventors have found that dexamethasone (e.g., at 1 μM, a glucocorticoid receptor agonist), ciglitazone and Fmoc-Leu (both used at 5 μM) (a PPAR agonist), and Bexarotene (e.g., at (3 μM) (a RXR antagonist) can enhance cellular reprogramming. Representative nuclear receptor ligands include, but are not limited to, estradiol (e.g., 17-beta estradiol), all-trans retinoic acid, 13-cis retinoic acid, dexamethasone, clobetasol, androgens, thyroxine, vitamin D3 glitazones, troglitazone, pioglitazone, rosiglitazone, prostaglandins, and fibrates (e.g., bezafibrate, ciprofibrate, gemfibrozil, fenofibrate and clofibrate). Furthermore, the activity of endogenous ligands (such as the hormones estradiol and testosterone) when bound to their cognate nuclear receptors is normally to upregulate gene expression. This upregulation or stimulation of gene expression by the ligand can be referred to as an agonist response. The agonistic effects of endogenous hormones can also be mimicked by certain synthetic ligands, for example, the glucocortocoid receptor anti-inflammatory drug dexamethasone. Agonist ligands function by inducing a conformation of the receptor which favors coactivator binding. (See, e.g., WO08011093A incorporate herein by reference.)

Inhibitors of GSK3 can include antibodies that bind, dominant negative variants of, and siRNA and antisense nucleic acids that target GSK3. Specific examples of GSK3inhibitors include, but are not limited to, Kenpaullone, 1-Azakenpaullone, CHIR99021, CHIR98014, AR-A014418 (see, e.g., Gould, et al., *The International Journal of Neuropsychopharmacology* 7:387-390 (2004)), CT 99021 (see, e.g., Wagman, *Current Pharmaceutical Design* 10:1105-1137 (2004)), CT 20026 (see, Wagman, supra), SB216763 (see, e.g., Martin, et al., *Nature Immunology* 6:777-784 (2005)), AR-A014418 (see, e.g., Noble, et al., *PNAS* 102: 6990-6995 (2005)), lithium (see, e.g., Gould, et al., *Pharmacological Research* 48: 49-53 (2003)), SB 415286 (see, e.g., Frame, et al., *Biochemical Journal* 359:1-16 (2001)) and TDZD-8 (see, e.g., Chin, et al., Molecular Brain Research, 137(1-2):193-201 (2005)). Further exemplary GSK3 inhibitors available from Calbiochem (see, e.g., Dalton, et al., WO2008/094597, herein incorporated by reference), include but are not limited to BIO (2'Z,3'£)-6-Bromoindirubin-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b] pyridin-3-yl]-4-pyrazin-2-yl-pyrrole-2,5-dione (GSK-3beta Inhibitor XI); TWSI 19 pyrrolopyrimidine compound (GSK3beta Inhibitor XII); L803 H-KEAPPAPPQSpP-NH2 (SEQ ID NO:1) or its Myristoylated form (GSK3beta Inhibitor XIII); 2-Chloro-1-(4,5-dibromo-thiophen-2-yl)-ethanone (GSK3beta Inhibitor VI); AR-AO144-18; SB216763; and SB415286. Residues of GSK3b that interact with inhibitors have been identified. See, e.g., Bertrand et al., *J. Mol Biol.* 333(2): 393-407 (2003). GSK3 inhibitors can activate, for example, the Wnt/β-catenin pathway. Many of β-catenin downstream genes co-regulate pluripotency gene networks. For example, a GSK inhibitor activates cMyc expression as well as enhances its protein stability and transcriptional activity. Thus, in some embodiments, GSK3 inhibitors can be used to stimulate endogenous Myc polypeptide expression in a cell, thereby eliminating the need for Myc expression to induce pluripotency.

Inhibitors of MEK can include antibodies to, dominant negative variants of, and siRNA and antisense nucleic acids that suppress expression of, MEK. Specific examples of MEK inhibitors include, but are not limited to, PD0325901, (see, e.g., Rinehart, et al., *Journal of Clinical Oncology* 22: 4456-4462 (2004)), PD98059 (available, e.g., from Cell Signaling Technology), U0126 (available, for example, from Cell Signaling Technology), SL 327 (available, e.g., from Sigma-Aldrich), ARRY-162 (available, e.g., from Array Biopharma), PD184161 (see, e.g., Klein, et al., *Neoplasia* 8:1-8 (2006)), PD184352 (CI-1040) (see, e.g., Mattingly, et al., *The Journal of Pharmacology and Experimental Therapeutics* 316:456-465 (2006)), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluate in Phase I and II clinical trials for cancer (see, e.g., Rinehart, et al., *Journal of Clinical Oncology* 22(22):4456-4462 (2004)). Other MEK inhibitors being evaluated in clinical trials include PD184352 (see, e.g., English, et al., *Trends in Pharmaceutical Sciences* 23(1):40-45 (2002)), BAY 43-9006 (see, e.g., Chow, et al., *Cytometry (Communications in Clinical Cytometry)* 46:72-78 (2001)), PD-325901 (also PD0325901), GSK1120212, ARRY-438162, RDEA119, AZD6244 (also ARRY-142886 or ARRY-886), RO5126766, XL518 and AZD8330 (also ARRY-704). (See, e.g., information from the National Institutes of Health located on the World Wide Web at clinicaltrials.gov as well as information from the Nation Cancer Institute located on the World Wide Web at cancer.gov/clinicaltrials.

TGF beta receptor (e.g., ALK5) inhibitors can include antibodies to, dominant negative variants of, and antisense nucleic acids that suppress expression of, TGF beta receptors (e.g., ALK5). Exemplary TGFβ receptor/ALK5 inhibitors include, but are not limited to, SB431542 (see, e.g., Inman, et al., *Molecular Pharmacology* 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., *Cancer Science* 96(11):791-800 (2005), and commercially available from, e.g., Toicris Bioscience); 2-(3-(6-Methylpyridin-2-yl)-1H-pyrazol-4-yl)-1, 5-naphthyridine, Wnt3a/BIO (see, e.g., Dalton, et al., WO2008/094597, herein incorporated by reference), BMP4 (see, Dalton, supra), GW788388 (-{4-[3-(pyridin-2-yl)-1H-pyrazol-4-yl]pyridin-2-yl}-N-(tetrahydro-2H-pyran-4-yl) benzamide) (see, e.g., Gellibert, et al., *Journal of Medicinal Chemistry* 49(7):2210-2221 (2006)), SM16 (see, e.g., Suzuki, et al., *Cancer Research* 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., *Xenobiotica* 38(3):325-339 (2008)), GW6604 (2-phenyl-4-(3-pyridin-2-yl-1H-pyrazol-4-yl)pyridine) (see, e.g., de Gouville, et al., *Drug News Perspective* 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., *Molecular Pharmacology* 65(3): 744-752 (2004)) and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., *J. Mol. Pharmacol.* 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

In view of the data herein showing the effect of inhibiting ALK5, it is believed that inhibition of the TGFβ/activin pathway will have similar effects. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGF beta receptor inhibitors can include antibodies to, dominant negative variants of and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGF beta receptors. (See, e.g., Wrzesinski, et al., *Clinical Cancer Research* 13(18):5262-5270 (2007); Kaminska, et al., *Acta Biochimica Polonica* 52(2):329-337 (2005); and Chang, et al., *Frontiers in Bioscience* 12:4393-4401 (2007).)

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., *Oncogene* 26:3311-3320 (2007); and Kataoka, et al., EP1992360, incorporated herein by reference.)

Inhibitors of the interaction of SMAD 2/3 and smad4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., *Oncogene* 24:3864-3874 (2005) and Zhao, et al., *Molecular Biology of the Cell,* 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to smad7-as PTO-oligonucleotides. (See, e.g., Miyazono, et al., U.S. Pat. No. 6,534,476, and Steinbrecher, et al., US2005119203, both incorporated herein by reference.)

Exemplary HDAC inhibitors can include antibodies that bind, dominant negative variants of, and siRNA and antisense nucleic acids that target HDAC. HDAC inhibitors include, but are not limited to, TSA (trichostatin A) (see, e.g., Adcock, *British Journal of Pharmacology* 150:829-831 (2007)), VPA (valproic acid) (see, e.g., Munster, et al., *Journal of Clinical Oncology* 25:18 S (2007): 1065), sodium butyrate (NaBu) (see, e.g., Han, et al., *Immunology Letters* 108:143-150 (2007)), SAHA (suberoylanilide hydroxamic acid or vorinostat) (see, e.g., Kelly, et al., *Nature Clinical Practice Oncology* 2:150-157 (2005)), sodium phenylbutyrate (see, e.g., Gore, et al., *Cancer Research* 66:6361-6369 (2006)), depsipeptide (FR901228, FK228) (see, e.g., Zhu, et al., *Current Medicinal Chemistry* 3(3):187-199 (2003)), trapoxin (TPX) (see, e.g., Furumai, et al., *PNAS* 98(1):87-92 (2001)), cyclic hydroxamic acid-containing peptide 1 (CHAP1) (see, Furumai supra), MS-275 (see, e.g., Carninci, et al., WO2008/126932, incorporated herein by reference)), LBH589 (see, e.g., Goh, et al., WO2008/108741 incorporated herein by reference) and PXD101 (see, Goh, supra). In general at the global level, pluripotent cells have more histone acetylation, and differentiated cells have less histone acetylation. Histone acetylation is also involved in histone and DNA methylation regulation. In some embodiments, HDAC inhibitors facilitate activation of silenced pluripotency genes.

Exemplary ERK inhibitors include PD98059 (see, e.g., Zhu, et al., *Oncogene* 23:4984-4992 (2004)), U0126 (see, Zhu, supra), FR180204 (see, e.g., Ohori, Drug News Perspective 21(5):245-250 (2008)), sunitinib (see, e.g., Ma, et al., US2008004287 incorporated herein by reference), sorafenib (see, Ma, supra), Vandetanib (see, Ma, supra), pazopanib (see, Ma, supra), Axitinib (see, Ma, supra) and PTK787 (see, Ma, supra).

Once expression cassettes have been introduced into the cells and/or the cells have been contacted with the one or more agents, the cells can be optionally screen for characteristics of pluripotent stem cells, thereby identifying those cells in a mixture that are pluripotent. Such cells can be, for example, isolated from the other cells and used further as appropriate.

III. Non-Pluripotent Cells

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells.

In some embodiments where an individual is to be treated with the resulting pluripotent cells, the individual's own non-pluripotent cells are used to generate pluripotent cells according to the methods of the invention.

Cells can be from, e.g., humans or non-human mammals. Exemplary non-human mammals include, but are not limited to, mice, rats, cats, dogs, rabbits, guinea pigs, hamsters, sheep, pigs, horses, and bovines.

IV. Transformation

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In some embodiments, the species of cell and protein to be expressed is the same. For example, if a mouse cell is used, a mouse ortholog is introduced into the cell. If a human cell is used, a human ortholog is introduced into the cell.

It will be appreciated that where two or more proteins are to be expressed in a cell, one or multiple expression cassettes can be used. For example, where one expression cassette is to express multiple polypeptides, a polycistronic expression cassette can be used.

A. Plasmid Vectors

In certain embodiments, a plasmid vector is contemplated for use to transform a host cell. In general, plasmid vectors containing replicon and control sequences which are derived from species compatible with the host cell are used in connection with these hosts. The vector can carry a replication site, as well as marking sequences which are capable of providing phenotypic selection in transformed cells.

B. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

i. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a ~36 kb, linear, double-stranded DNA virus, allows substitution of large pieces of adenoviral DNA with foreign sequences up to 7 kb (Grunhaus et al., Seminar in Virology, 200(2):535-546, 1992)).

ii. AAV Vectors

The nucleic acid may be introduced into the cell using adenovirus assisted transfection. Increased transfection efficiencies have been reported in cell systems using adenovirus coupled systems (Kelleher and Vos, *Biotechniques,* 17(6): 1110-7, 1994; Cotten et al., *Proc Natl Acad Sci USA,* 89(13):6094-6098, 1992; Curiel, *Nat Immun,* 13(2-3):141-64, 1994.). Adeno-associated virus (AAV) is an attractive vector system as it has a high frequency of integration and it can infect non-dividing cells, thus making it useful for delivery of genes into mammalian cells, for example, in tissue culture (Muzyczka, *Curr Top Microbiol Immunol,* 158:97-129, 1992) or in vivo. Details concerning the generation and use of rAAV vectors are described in U.S. Pat. Nos. 5,139,941 and 4,797,368, each incorporated herein by reference.

iii. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller et al., *Am. J. Clin. Oncol.,* 15(3):216-221, 1992).

In order to construct a retroviral vector, a nucleic acid (e.g., one encoding gene of interest) is inserted into the viral genome in the place of certain viral sequences to produce a virus that is replication-defective. To produce virions, a packaging cell line containing the gag, pol, and env genes but without the LTR and packaging components is constructed (Mann et al., Cell, 33:153-159, 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986; Mann et al., Cell, 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., Virology, 67:242-248, 1975).

Lentiviruses are complex retroviruses, which, in addition to the common retroviral genes gag, pol, and env, contain other genes with regulatory or structural function. Lentiviral vectors are well known in the art (see, for example, Naldini et al., Science, 272(5259):263-267, 1996; Zufferey et al., Nat Biotechnol, 15(9):871-875, 1997; Blomer et al., J. Virol., 71(9):6641-6649, 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iv. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., Proc. Nat'l Acad. Sci. USA, 86:9079-9083, 1989). Using antibodies against major histocompatibility complex class I and class II antigens, they demonstrated the infection of a variety of human cells that bore those surface antigens with an ecotropic virus in vitro (Roux et al., 1989).

C. Vector Delivery and Cell Transformation

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art. Such methods include, but are not limited to, direct delivery of DNA such as by ex vivo transfection (Wilson et al., Science, 244:1344-1346, 1989, Nabel and Baltimore, Nature 326: 711-713, 1987), optionally with Fugene6 (Roche) or Lipofecyamine (Invitrogen), by injection (U.S. Pat. Nos. 5,994, 624, 5,981,274, 5,945,100, 5,780,448, 5,736,524, 5,702,932, 5,656,610, 5,589,466 and 5,580,859, each incorporated herein by reference), including microinjection (Harland and Weintraub, J. Cell Biol., 101:1094-1099, 1985; U.S. Pat. No. 5,789,215, incorporated herein by reference); by electroporation (U.S. Pat. No. 5,384,253, incorporated herein by reference; Tur-Kaspa et al., Mol. Cell. Biol., 6:716-718, 1986; Potter et al., Proc. Nat'l Acad. Sci. USA, 81:7161-7165, 1984); by calcium phosphate precipitation (Graham and Van Der Eb, Virology, 52:456-467, 1973; Chen and Okayama, Mol. Cell. Biol., 7(8):2745-2752, 1987; Rippe et al., Mol. Cell. Biol., 10:689-695, 1990); by using DEAE-dextran followed by polyethylene glycol (Gopal, Mol. Cell. Biol., 5:1188-1190, 1985); by direct sonic loading (Fechheimer et al., Proc. Nat'l Acad. Sci. USA, 84:8463-8467, 1987); by liposome mediated transfection (Nicolau and Sene, Biochim. Biophys. Acta, 721:185-190, 1982; Fraley et al., Proc. Nat'l Acad. Sci. USA, 76:3348-3352, 1979; Nicolau et al., Methods Enzymol., 149:157-176, 1987; Wong et al., Gene, 10:87-94, 1980; Kaneda et al., Science, 243:375-378, 1989; Kato et al., J Biol. Chem., 266:3361-3364, 1991) and receptor-mediated transfection (Wu and Wu, Biochemistry, 27:887-892, 1988; Wu and Wu, J. Biol. Chem., 262: 4429-4432, 1987); each incorporated herein by reference); and any combination of such methods.

V. Culturing of Cells

Cells to be induced to pluripotency can be cultured according to any method known in the art. General guidelines can be found in, e.g., Maherali, et al., Cell Stem Cell 3:595-605 (2008).

In some embodiments, the cells are cultured in contact with feeder cells. Exemplary feeder cells include, but are not limited to fibroblast cells, e.g., mouse embryonic fibroblast (MEF) cells. Methods of culturing cells on feeder cells is known in the art.

In some embodiments, the cells are cultured in the absence of feeder cells. Cells, for example, can be attached directly to a solid culture surface (e.g., a culture plate), e.g., via a molecular tether. The inventors have found that culturing cells induced to pluripotency have a much greater efficiency of induction to pluripotency (i.e., a greater portion of cells achieve pluripotency) when the cells are attached directly to the solid culturing surface compared the efficiency of otherwise identically-treated cells that are cultured on feeder cells. Exemplary molecular tethers include, but are not limited to, matrigel, an extracellular matrix (ECM), ECM analogs, laminin, fibronectin, or collagen. Those of skill in the art however will recognize that this is a non-limiting list and that other molecules can be used to attach cells to a solid surface. Methods for initial attachment of the tethers to the solid surface are known in the art.

As used in this "culturing" section, "cells to be induced to pluripotency" are induced by any method in the art, including, but not limited to the methods described in this application.

VI. Uses for Pluripotent Cells

The present invention allows for the further study and development of stem cell technologies, including but not limited to, prophylactic or therapeutic uses. For example, in some embodiments, cells of the invention (either pluripotent cells or cells induced to differentiate along a desired cell fate) are introduced into individuals in need thereof, including but not limited to, individuals in need of regeneration of an organ, tissue, or cell type. In some embodiments, the cells are originally obtained in a biopsy from an individual; induced into pluripotency as described herein, optionally induced to differentiate (for examples into a particular desired progenitor cell) and then transplanted back into the individual. In some embodiments, the cells are genetically modified prior to their introduction into the individual.

In some embodiments, the pluripotent cells generated according to the methods of the invention are subsequently induced to form, for example, hematopoietic (stem/progenitor) cells, neural (stem/progenitor) cells (and optionally, more differentiated cells, such as subtype specific neurons, oligodendrocytes, etc), pancreatic cells (e.g., endocrine progenitor cell or pancreatic hormone-expressing cells), hepatocytes, cardiovascular (stem/progenitor) cells (e.g., cardiomyocytes, endothelial cells, smooth muscle cells), retinal cells, etc.

A variety of methods are known for inducing differentiation of pluripotent stem cells into desired cell types. A non-limiting list of recent patent publications describing methods for inducing differentiation of stem cells into various cell fates follows: U.S. Patent Publication No. 2007/0281355; 2007/0269412; 2007/0264709; 2007/0259423; 2007/0254359; 2007/0196919; 2007/0172946; 2007/0141703; 2007/0134215.

A variety of diseases may be ameliorated by introduction, and optionally targeting, of pluripotent cells of the invention to a particular injured tissue. Examples of disease resulting from tissue injury include, but are not limited to, neurodegeneration disease, cerebral infarction, obstructive vascular disease, myocardial infarction, cardiac failure, chronic obstructive lung disease, pulmonary emphysema, bronchitis, interstitial pulmonary disease, asthma, hepatitis B (liver damage), hepatitis C (liver damage), alcoholic hepatitis (liver damage), hepatic cirrhosis (liver damage), hepatic insufficiency (liver damage), pancreatitis, diabetes mellitus, Crohn disease, inflammatory colitis, IgA glomerulonephritis, glomerulonephritis, renal insufficiency, decubitus, burn, sutural wound, laceration, incised wound, bite wound, dermatitis, cicatricial keloid, keloid, diabetic ulcer, arterial ulcer and venous ulcer.

The polypeptides described herein (e.g., one or more of a Klf polypeptide, an Oct polypeptide, a Myc polypeptide, and a Sox polypeptide) are themselves useful therapeutic agents alone, or in combination as described herein. For example, the polypeptides, or combinations thereof, are useful for reducing tissue damage and thus can be administered to treat, ameliorate, or prevent tissue damage. In some embodiments, a compound of the invention is administered to an individual having, or at risk of having tissue damage to an internal organ. Internal organs include, but are not limited to, brain, pancreas, liver, intestine, lung, kidney, or heart, wounding, e.g., by burn or cut. For example, in some embodiments, the compounds of the invention are effective in reducing infarction size in reperfusion following ischemia. Thus, a protein of the invention can be administered to individuals at risk of having, having, or who have had, a stroke. Similarly, a protein of the invention can be administered to individuals at risk of having, having, or who have had, a heart attack or cardiac damage.

The agents described herein (e.g., an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor.) are also useful therapeutic agents alone, or in combination with each other as described herein. For example, the agents, or combinations thereof, are useful for reducing tissue damage and thus can be administered to treat, ameliorate, or prevent tissue damage. In some embodiments, an agent of the invention is administered to an individual having, or at risk of having tissue damage to an internal organ. Internal organs include, but are not limited to, brain, pancreas, liver, intestine, lung, kidney, or heart, wounding, e.g., by burn or cut. For example, in some embodiments, the agents of the invention are effective in reducing infarction size in reperfusion following ischemia. Thus, an agent of the invention can be administered to individuals at risk of having, having, or who have had, a stroke. Similarly, an agent of the invention can be administered to individuals at risk of having, having, or who have had, a heart attack or cardiac damage.

Active compounds described herein also include the salts, hydrates, solvates and prodrug forms thereof. The compounds of the present invention also include the isomers and metabolites thereof. Certain compounds of the present invention possess asymmetric carbon atoms (optical centers) or double bonds; the racemates, diastereomers, geometric isomers and individual isomers are all intended to be encompassed within the scope of the present invention. For example, the compound of the present invention can be the R-isomer or the S-isomer, or a mixture thereof. In addition, the compound of the present invention can be the E-isomer or the Z-isomer, or a combination thereof.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts. In some embodiments, the present invention provides the hydrochloride salt. In other embodiments, the compound is ellipticine hydrochloride.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present invention.

The compounds of the present invention can be made by a variety of methods known to one of skill in the art (see *Comprehensive Organic Transformations* Richard C.

Larock, 1989). One of skill in the art will appreciate that other methods of making the compounds are useful in the present invention.

Administration of cells or compounds described herein is by any of the routes normally used for introducing pharmaceuticals. The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 17$^{th}$ ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intrathecally or into the eye (e.g., by eye drop or injection). The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time, i.e., to ameliorate a condition of the subject. The optimal dose level for any patient will depend on a variety of factors including the efficacy of the specific modulator employed, the age, body weight, physical activity, and diet of the patient, and on a possible combination with other drug. The size of the dose also will be determined by the existence, nature, and extent of any adverse side-effects that accompany the administration of a particular compound or vector in a particular subject. Administration can be accomplished via single or divided doses.

VII. Screening for Agents that Induce Pluripotent Stem Cell Development

The present invention provides for methods of screening for agents that can "replace" one of the four iPS transcription factors (i.e., an Oct polypeptide, a Klf polypeptide, a Myc polypeptide, and a Sox polypeptide), or alternatively can replace an Oct polypeptide, a Klf polypeptide, or a Sox polypeptide in cells where Myc is not necessary to reprogram cells into pluripotent cells (Nakagawa, M. et al. *Nature Biotechnol.* 26, 101-106 (2007); Wernig, M., Meissner, A., Cassady, J. P. & Jaenisch, R. *Cell Stem Cell* 2, 10-12 (2008)) or alternatively improve the efficiency of induction to pluripotency.

In some embodiments, the methods comprise introducing one or more expression cassettes for expression of at least one of, but not all of, an Oct polypeptide, a Klf polypeptide, a Myc polypeptide, and a Sox polypeptide into non-pluripotent cells to generate transfected cells; subsequently contacting the transfected cells to a library of different agents; screening the contacted cells for pluripotent stem cell characteristics; and correlating the development of stem cell characteristics with a particular agent from the library, thereby identifying an agent that stimulates dedifferentiation of cells into pluripotent stem cells. In some embodiments, the cells are contacted with at least one of an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor as well as one or more members of a small molecule or other agent library to identify a library member that induces or improves induction of cells to pluripotency. Thus, mixtures of non-pluripotent cells and at least one (e.g., 1, 2, 3, 4, 5 or more of) an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor are provided in the present invention.

The agents in the library can be any small chemical compound, or a biological entity, such as a protein, sugar, nucleic acid or lipid. Typically, test agents will be small chemical molecules and peptides. Essentially any chemical compound can be used as a potential agent in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential iPS replacement agents (potentially acting to replace one of the iPS proteins). Such "combinatorial chemical libraries" are then screened in one or more assays, as described herein, to identify those library members (particular chemical species or subclasses) that display a desired characteristic activity, i.e., such as inducing pluripotent stem cell characteristics in cells that express some, but not all of, an Oct polypeptide, a Klf polypeptide, a Myc polypeptide, and a Sox polypeptide.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Cells contacted with the agents, and optionally expressing some but not all of an Oct polypeptide, a Klf polypeptide, a Myc polypeptide, and a Sox polypeptide (e.g., combinations of one, two or three of an Oct polypeptide, a Klf polypeptide, a Myc polypeptide, and a Sox polypeptide), can then be screened for the development of pluripotent cells, e.g., by screening for one or more pluripotent stem cell characteristics. Initial screens can be designed by transforming the cells to be screened with an expression cassette comprising promoter elements known to be activated in pluripotent stem cells (optionally, but not other cells) operably linked to a selectable or otherwise identifiable marker. For example, a detectable marker such as GFP or other reporter system can be used. Exemplary promoter elements known to be activated in pluripotent cells include, but are not limited to, Oct4, Nanog, SSEA1 and ALP promoter sequences. Cells can also be screened for expression of other pluripotent cell markers (e.g., by immunofluorescence, etc.) as are known in the art, including, but not limited to Nanog, SSEA1 and ALP. In some embodiments, cell morphology is examined.

In some embodiments, the cells are cultured in the presence of a MAPK/ERK kinase (MEK) inhibitor. The inventors have found that the presence of a MEK inhibitor results in both inhibition of growth of non-pluripotent cells and stimulation of growth of pluripotent stem cells. This effect therefore magnifies the "signal" of the screen and allows for more efficient and sensitive detection of agents that induce reprogramming of cells into pluripotent stem cells. A wide variety of MEK inhibitors are known, including but not limited to, PD0325901 (see, e.g., Thompson, et al., Current Opinion in Pharmacology 5(4): 350-356 (2005)); MEK Inhibitor U0126 (Promega), ARRY-886 (AZD6244) (Array Biopharma); PD98059 (Cell Signaling Technology); and Amino-thio-acrylonitriles (U.S. Pat. No. 6,703,420). Other MEK inhibitors are described in, e.g., U.S. Pat. No. 6,696, 440 and WO 04/045617, among others.

VIII. Cell Mixtures

As discussed herein, the present invention provides for non-pluripotent cells in a mixture with one or more compound selected from the group consisting of an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor. In some embodiments, the compound is in the mixture at a concentration sufficient to induce or improve efficiency of induction to pluripotency. For example, in some embodiments, the compounds are in a concentration of at least 0.1 nM, e.g., at least 1, 10, 100, 1000, 10000, or 100000 nM, e.g., between 0.1 nM and 100000 nM, e.g., between 1 nM and 10000 nM, e.g., between 10 nM and 10000 nM. In some embodiments, the mixtures are in a synthetic vessel (e.g., a test tube, Petri dish, etc.). Thus, in some embodiments, the cells are isolated cells (not part of an animal). In some embodiments, the cells are isolated from an animal (human or non-human), placed into a vessel, contacted with one or more compound as described herein. The cells can be subsequently cultured and optionally, inserted back into the same or a different animal, optionally after the cells have been stimulated to become a particular cell type or lineage.

As explained herein, in some embodiments, the cells comprise an expression cassette for heterologous expression of at least one or more of an Oct polypeptide, a Myc polypeptide, a Sox polypeptide and a Klf polypeptide. In some embodiments, the cells do not include an expression cassette to express any of the Oct, Myc, Sox of Klf polypeptides. Cells with or without such expression cassettes are useful, for example, screening methods as described herein.

Examples of non-pluripotent cells include those described herein, including but not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells.

The present invention also provides mixtures (with, or optionally without cells) of an agent that inhibits H3K9 methylation (including but not limited to BIX-01294) with a compound selected from at least one of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor. In some including but not limited to embodiments, the agent and at least one compound listed above is at a concentration as described above. Such mixtures are useful, for example, as "pre-mixes" for induction of pluripotency in cells.

IX. Kits

The present invention also provides kits, e.g., for use in inducing or improving efficiency of induction of pluripotency in cells. Such kits can comprise one of more compound selected from the group consisting of an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor. In some embodiments, the kits comprise an agent that inhibits H3K9 methylation (including but not limited to BIX-01294) and a second compound (separate or mixed with agent that inhibits H3K9 methylation) selected from at least one of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor.

In some embodiments, the kits further comprise non-pluripotent cells. Examples of non-pluripotent cells include those described herein, including but not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells.

EXAMPLE

Example 1

Toward identifying conditions that can replace viral transduction of oncogenic transcription factors (e.g. cMyc and Oct4 (Hochedlinger, K. et al., Cell 121, 465-477 (2005)) and enhance reprogramming efficiency, we sought to exploit combination of two approaches: one was to examine a defined progenitor cell type based on the notion that certain accessible adult progenitor cells may endogenously express at certain level some of the required genes for inducing pluripotency and/or the loci of these genes may be less silenced so that such progenitor cells might be more efficiently reprogrammed and/or with less genetic manipulations; the other approach was to screen small molecules that may be able to replace viral integration of specific transcription factor and/or promote reprogramming process.

Among various adult stem/progenitor cells that are accessible from different tissues, we initially focused our efforts on neural progenitor cells for the following reasons: (i) In contrast to heterogeneous primary fibroblast culture (e.g., MEF) which may contain various types of stem/progenitor cells, neural progenitor cells are relatively defined population of cells and can be clonally expanded under chemically defined conditions. (ii) Neural progenitor cells endogenously express specific Sox genes (e.g. Sox1 or Sox2), which, although is at lower level than overexpression, might be sufficient for generating iPS cells. (iii) Neural progenitor cells or Sox gene expressing cells may be isolated from other tissues (Fernandes, K. J. L. et al., Nature Cell Biology 6, 1082-1093 (2004); Seaberg, R. M. et al., Nature Biotechnol. 22, 1115-1124 (2004)) and expanded in vitro. Therefore, defined neural progenitor cells represent an excellent model system to address above questions in reprogramming process/mechanism. To establish an unlimited, highly reproducible and defined source of neural progenitor cells that can be used in high throughput screens, we chose to use mESC-derived neural progenitor cells that contain a GFP-IRES-Puro/GiP reporter under control of the Oct4 regulatory elements, since mESCs can be grown in large quantity and their differentiation to a homogenous population of neural progenitor cells is well defined (Conti, L. et al., PLoS Biol. 3, e283 (2005)), as well as the validated reporter activity (Ying, Q. L. et al., Nature 416, 545-548 (2002)) can facilitate facile assay detection.

The reporter neural progenitor cells were generated using a well established protocol by differentiating the Oct4-GiP mESCs grown in monolayer on gelatin in a chemically defined medium/CDM condition in the absence of serum and other growth factors/cytokines at low cell density for eight days, followed by neurophere formation and subsequent serial passaging in single cells in neural cell expansion media supplemented with 10 ng/ml of bFGF and EGF in monolayer for over six passages/24 days. The resulting neural progenitor cells were homogenous by cell morphology and neural marker expression, and were confirmed to be GFP negative and puromycin sensitive. Such neural progenitor cells plated in monolayer in conventional mESC growth media were transduced with combinations of four, three, or two of the four factors, followed by treating the transduced cells with individual small molecules from a small known drug collection in a typical 6-well format. The compound treatment and culture were continued for additional ten days before puromycin was added. The number of green and puro-resistant colonies was counted at day 14. In comparison to the only four-gene transduced neural cells as the positive control, compound conditions that generated more green colonies than the corresponding gene-only conditions were picked as primary hits. To further confirm these primary hit conditions, we chose to use a late passage of mouse CNS neural progenitor cells (Do, J. T. et al., Stem Cells 25, 1013-1020 (2007)) that were derived from fetal brain of $OG2^{+/-}/ROSA26^{+/-}$ transgenic mice (which contain an Oct4-GFP reporter) and expanded in monolayer under the same neural CDM condition as the above with 10 ng/ml of bFGF and EGF. Such cells truly from a non-pluripotent tissue would be devoid of concerns of any contaminating ES cell in the above screening system, which is although highly unlikely with all appropriate controls. Similar culture conditions and reprogramming assays were performed using the OG2 neural progenitor cells except that puromycin was not used and green colonies were picked out and characterized by staining of Nanog, SSEA1 and ALP. We found that almost all of the green colonies that can be identified at day 12-14 can be expanded to long-term stable iPS cells that are indistinguishable from the classic mESCs by morphology and typical pluripotency marker expression.

We first focused our characterization efforts on two new conditions that could be reconfirmed using the fetal neural progenitor cells. Just as hypothesized that certain tissue-specific progenitor cells with endogenous expression of certain relevant reprogramming genes may require less exogenous genetic manipulation to generate iPS cells, we found that viral transduction of only Oct4 and Klf4 together is sufficient to generate iPS cells from neural progenitor cells in 10-14 days. While such reprogramming efficiency (1-2 GFP colonies per $3.5 \times 10^4$ cells) is lower than conditions with additional Sox2 and cMyc viral transduction (8-10 GFP colonies per $3.5 \times 10^4$ cells) (FIG. 1), it is interesting that the reprogramming kinetics by the two genes only (Oct4 and Klf4) is not significantly slower than that by the original four genes. This is in contrast to the recent observations that omitting cMyc in generating iPS cells from MEFs is significantly slower (e.g. additional 2 weeks) than the condition having cMyc overexpression even the embryonic fibroblasts endogenously express cMyc. Most interestingly, we found that a small molecule, BIX01294 (Kubicek, S. et al., Molecular Cell 25, 473-481 (2007)) that specifically inhibits G9a (a histone methyltransferase for H3K9me2), can significantly improve the reprogramming efficiency to or higher than the level of using viral transduction of all four factors, while it didn't significantly shorten the kinetics of reprogramming. The reprogramming event is typically assayed by the ability of identifying the iPS cell colonies, which is influenced by many factors, including the methods of cell culture, cell identification and/or selection, as well as the input cell type, number, and reprogramming efficiency and kinetics. Consequently, a requirement for any given gene for reprogramming is relative to that specific setting and largely depends on the reprogramming efficiency/kinetics. In this regard, this single small molecule, BIX01294, functionally replaced viral transduction of cMyc and Sox2 to large extent.

GFP+ iPS cell colonies readily appeared 12 days after OG2 neural progenitor cells were transduced with Oct4/Klf4 retroviruses and treated with BIX01294. Day 14 iPS cells generated from Oct4-Klf4 viral transduction and BIX01294 treatment can be readily expanded in the conventional mESC culture condition on MEF feeder cells in the presence of LIF without the requirement of continued BIX01294 treatment. iPS cells generated by Oct4/Klf4 viral transduction and BIX01294 treatment can long-term self-renew on MEF feeders in the mESC growth media without continued BIX01294 treatment. They grow as compact and domed colonies. These iPS cells maintain characteristic mESC-colony morphology, homogenously express typical pluripotency markers in comparable level as mESCs, including Oct4, Nanog, SSEA1 and ALP by immunocytochemistry, histostaining and RT-PCR analysis. Furthermore, such iPS cells, which had been serially passaged over 10 passages, can effectively differentiate into characteristic neurons (βIII-tubulin), beating cardiomyocytes (cardiac troponin) and pancreatic or hepatic cells (Pdx1 or Albumin), derivatives of the three primary germ layers under standard embryoid body or directed differentiation methods. And most importantly, such iPS cells can efficiently incorporate into the ICM of a blastocyst after aggregation with an 8-cell embryo, lead to a high-grade chimerism after the aggregated embryos were transplanted into mice, and contribute to the germ line in vivo. These in vitro and in vivo characterizations confirm that the iPS cells generated by Oct4 and Klf4 viral transduction with simultaneous BIX01294 treatment are morphologically, functionally and by typical pluripotency marker expression indistinguishable from the original four-factor iPS cells and the classic mESCs.

Figure 2:
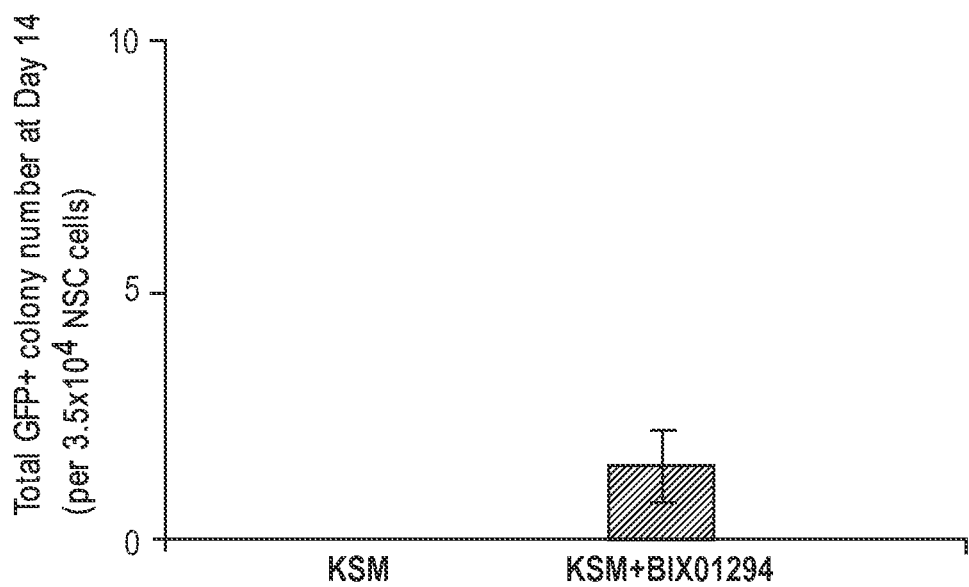
FIG. 2 Generation of iPS cells from primary neural progenitor cells by Klf4/Sox2/c-Myc viral transduction and BIX01294 treatment. The number of GFP+ iPS cell colonies generated from $3.5 \times 10^4$ primary OG2 neural progenitor cells by retroviral transduction of Klf4/Sox2/c-Myc with or without BIX01294 treatment.

One question is whether expression of Oct4, Sox2, Klf4 and cMyc, regardless of endogenously or exogenously, would be a prerequisite for generating iPS cells. Interestingly, recent reprogramming studies on generating human iPS cells from fibroblasts have shown while exogenous expression of Klf4 and cMyc are functionally exchangeable with Nanog and Lin28, expression of Oct4 and Sox2 seems to be required so far from all published iPS cell studies. Interestingly, we found that viral transduction of Klf4, Sox2, and cMyc with simultaneous BIX01294 treatment in the absence of Oct4 expression can also generate iPS cells (FIG. 2) while viral transduction of such three factors/KSM alone failed to produce any iPS cell colony under our assay conditions. Similarly, such KSM-BIX01294 generated iPS cells can be stably expanded and long-term self-renew on MEF feeders in the conventional mESC growth conditions over passages without BIX01294, maintain the characteristic mESC morphologies, homogenously express typical pluripotency markers, including ALP, Oct4, Nanog and SSEA1, and differentiate into cells in the three germ layers in vitro. It should be noted that the reprogramming efficiency in the absence of Oct4 expression is relatively low.

Finally, we observed that the application of a specific small molecule inhibitor of MEK, PD0325901, to late stage of reprogramming (e.g. after Oct4-GFP activation) can serve as an excellent selection strategy for generating iPS cells. Due to the very low efficiency of reprogramming, iPS cells are typically selected out by utilizing reporter (e.g. Neo/Puro or GFP) that is under control of the regulatory elements of a pluripotency marker using genetically modified somatic cell lines, or manually picked out based on cell morphology. While the later method applicable to genetically unmodified cells is better suited for ultimate clinical application of iPS cells, it is a much more tedious and less reliable technique that typically requires picking and propagating over several passages many colonies, only a small fraction of which would become true iPS cells efficiently. This is partly because that large percentage of similarly looking colonies may be partially reprogrammed cells and/or simply transformed cells, which grow rapidly and may interfere with growth and reprogramming of iPS cells. Consequently, having an alternative selection strategy for genetically unmodified cells would be highly desirable. We found that PD0325901 inhibits growth of non-iPS cells while it effectively promotes growth and stable reprogramming of iPS cells, leading to larger and more homogenous colonies of iPS cells. This observation might be partly due to the mechanism that MEK activity is required for cell cycle progression of somatic cells, while mESCs lack of such restriction for growth and inhibition of MEK also inhibits differentiation of mESCs (contributing to further stabilization of the iPS cell state).

The results presented here have a number of important implications. (1) The lower endogenous expression level (than overexpression) of critical genes required for reprogramming by (tissue-specific progenitor) somatic cells may be sufficient to replace the corresponding exogenous gene expression via viral transduction for generating iPS cells. This points to an alternative strategy of generating iPS cells from somatic cells using less genetic manipulation by exploiting practically accessible cells that endogenously express certain relevant reprogramming genes via an intrinsic tissue specificity and/or ex vivo culture manipulation. (2) This is a proof-of-principle demonstration that small molecules can be identified from rationally designed cell-based screens to functionally replace viral transduction of certain transcription factor(s), improve reprogramming efficiency, or serve as a selection condition in generating iPS cells. Not only may such pharmacological approach for replacing specific genetic manipulation substantially reduce risks associated with insertion of oncogenes (e.g. cMyc and Oct4) and insertional mutagenesis, but also it opens up the possibility of enabling a precisely controlled and highly efficient reprogramming process by defined small molecules. This is especially important for studying the molecular mechanism of reprogramming, which currently is largely intractable due to its very low efficiency and slow kinetics. (3) In contract to the gain-of-function approach in generating iPS cells, the highly effective use of those specific small molecule inhibitors suggests that loss-of-function of specific genes may be at least equally important and effective in generating iPS cells. More importantly, the function of BIX01294 defines a specific epigenetic mechanism/target, i.e. inhibition of G9a-mediated H3K9me2, in generating iPS cells. This is consistent with the previous findings that the repressive H3K9 methylation is associated with Oct4 inactivation during differentiation (Feldman, N. et al., *Nature Cell Biology* 8, 188-194 (2006)), and histone lysine methylation, although robust, is dynamic and regulated by HMTases and lysine demethylases. BIX01294 may function to facilitate shifting the epigenetic balance from a silenced state of Oct4 to an active transcription. (4) Exemplified by using MEK inhibitor for facile selection of iPS cells, exploiting the differences between somatic cells and ESCs by small molecules represents an alternative/attractive strategy for selecting iPS cells. Finally, it is conceivable that the strategies and small molecules reported here can be further explored for improved approaches and better mechanistic understanding of generating iPS cells, and combined with additional small molecules (that can replace the function of remaining transduced transcription factors and improve reprogramming) as well as other non-genetic methods (e.g. protein transduction) to ultimately allow generation of iPS cells in high efficiency in a completely chemically defined condition without any genetic modification.

Methods.

Neural progenitor cell culture. Neural progenitor cells were derived from mESCs or mouse fetal brains according to the protocol reported by Conti et al (Conti, L. et al., *PLoS Biol.* 3, e283 (2005)). Briefly, mESCs were plated onto a 0.1% gelatin-coated dish at $1 \times 10^4$ cells/cm$^2$ in the neural induction medium (50% DMEM/F12 basal medium, 50% Neurobasal medium, 0.5×N2, 0.5×B27, 1× Glutamax, 50 ug/ml BSA) and differentiated for 7-8 days. The formed neural rosettes were then trypsinized into single cells and replated into an Ultra-Low Attachment dish (Corning) to form neurosphere in the neural progenitor cell expansion medium (DMEM/F12, 1×N2, 10 ng/ml bFGF, 10 ng/ml EGF, 50 ug/ml BSA). After three days in suspension neurospheres were re-attached to a gelatin-coated dish and further differentiated for 4-6 days before they were further passaged in single cells and grown in monolayer on gelatin-coated dishes in the neural progenitor cell expansion medium for over 5-6 passages.

Neurospheres from brains of 12.5 to 16.5 dpc ROSA26/OG2 heterozygous fetuses were generated as previously described (Do, J. T. et al., *Stem Cells* 25, 1013-1020 (2007)). Briefly, the cortex was dissected, enzymatically dissociated, and passed through a 70 μm nylon mesh (Falcon; Franklin Lakes, N.J.). Neural cells were further purified by centrifugation in 0.9 M sucrose in 0.5×HBSS at 750 g for 10 min and in 4% BSA in EBSS solution at 200 g for 7 min. Such cells were further grown in suspension to form neurospheres and subsequently serially passaged in monolayer on gelatin-coated dishes in the neural progenitor cell expansion medium as described above. Animal experiments were approved and performed according to the Animal Protection Guidelines of the Government of Max Planck Society, Germany.

Retrovirus Transduction.

The murine cDNAs for Oct4, Klf4, Sox2 and c-Myc were cloned into the pMSCV retroviral vector and verified by sequencing. The pMX-based retroviral vectors were obtained from Addgene. The virus production and transduction were performed as described 2-3.

iPS Cell Induction from Neural Progenitor Cells.

mESC-derived or primary OG2 mouse neural progenitor cells were plated into Matrigel (1:50, BD Biosciences) coated 6-well plates at $3.5 \times 10^4$ cells/well in the neural progenitor cell expansion media. After one day these cells were transduced with retrovirus for overnight, and the medium was changed into the mESC growth media [DMEM, 5% FBS, 10% KSR, 1× non-essential amino acids (Gibco), 2 mM L-glutamine (Gibco), 0.1 mM β-mercaptoethanol (Gibco) and $10^3$ unit/ml LIF (Chemicon)] with or without BIX01294 (0.5-1 μM). GFP-positive iPS cell colonies appeared after 9-14 days, and were picked out and expanded on MEF feeder cells with the mESC growth media.

Characterization Assays.

ALP staining was performed as instructed by the Alkaline Phosphatase Detection Kit (Chemicon). Cells were fixed in 4% paraformaldehyde, washed three times by PBS, and then incubated in PBS containing 0.3% TritonX-100 (Sigma) and 10% normal donkey serum (Jackson ImmunoResearch) for 30 min at room temperature. The cells were then incubated with primary antibody overnight at 4° C.: mouse anti-Oct4 antibody, mouse anti-SSEA1 antibody (1:200, Santa Cruz), rabbit anti-Sox2 antibody (1:200, Chemicon), rabbit anti-Nanog antibody (AbCam), rabbit anti-Pdx1 (1:200, from Dr. C. Wright), mouse anti-βIII-tubulin antibody (1:500, Covance), mouse anti-cardiac troponin T (1:200, DSHB), rabbit anti-Albumin antibody (DAKO). After washing, cells were further incubated with secondary antibodies: Alexa Fluoro555 donkey anti-mouse IgG or Alexa Fluoro555 donkey anti-rabbit IgG (1:500, Invitrogen) for 30 min at RT. Nuclei were detected by DAPI (Sigma) staining. Images were captured by Nikon TE2000-U.

Aggregation of iPS Cells with Zona-Free Embryos.

iPS cells were aggregated with denuded post-compacted eight-cell stage embryos to obtain aggregate chimera. Eight-cell embryos (B6C3F1) flushed from females at 2.5 dpc were cultured in microdrops of KSOM medium (10% FCS) under mineral oil. Clumps of iPS cells (10-20 cells) after short treatment of trypsin were chosen and transferred into microdrops containing zona-free eight-cell embryos. Eight-cell embryos aggregated with iPS cells were cultured overnight at 37° C., 5% CO2. Aggregated blastocysts developed from eight-cell stage were transferred into one uterine horn of a 2.5 dpc pseudopregnant recipient.

Example 2

Somatic cells can be induced into pluripotent stem cells (iPSC) with a combination of four transcription factors, Oct4/Sox2/Klf4/c-Myc or Oct4/Sox2/Nanog/LIN28. This provides an enabling platform to obtain patient specific cells for various therapeutic and research applications. However, several problems remain for this approach to be therapeutically relevant due to drawbacks associated with efficiency and viral genome-integration. As explained above, neural progenitor cells (NPCs) transduced with Oct4/Klf4 can be reprogrammed into iPSCs. However, NPCs express Sox2 endogenously, possibly facilitating reprogramming in the absence of exogenous Sox2. In this study, we identified a small molecule combination, BIX-01294 and BayK8644, that enables reprogramming of Oct4/Klf4 transduced mouse embryonic fibroblasts, which do not endogenously express the factors essential for reprogramming. This study demonstrates that small molecules identified through a phenotypic screen can compensate for viral transduction of critical factors, such as Sox2, and improve reprogramming efficiency.

This example is aimed to assess if small molecules can replace specific viral transduction to obtain iPSCs from a general cell lineage, in which none of the TFs deemed essential for reprogramming, Oct4, Sox2 and Klf4, are expressed. Hence, mouse embryonic fibroblasts (MEFs) were used. Finding a small molecule that could replace one of these TFs in the induction of MEF reprogramming might lead to the identification of general pathways involved in this process. Such chemical strategy might be more amenable for therapeutic application. Consequently, we screened a collection of known drugs to identify small molecules that can enable the generation of iPSCs from MEFs transduced with OK, and thus, could compensate for the lack of Sox2 overexpression. Through the different screens performed we identified that a combination of BIX with Bayk8644 (BayK), a L-channel calcium agonist (Schramm, M. et al., *Nature*, 303:535-537 (1983)) was one of the most effective. Bayk was of interest because it exerts its effect upstream in cell signaling pathways, and does not directly cause epigenetic modifications. It is likely that this type of molecule, such as BayK or activators of the Wnt signaling pathway (Marson, A. et al., *Cell Stem Cell*, 3:132-135 (2008)), can be exploited to induce reprogramming in a more specific manner than molecules acting directly at the epigenetic level causing DNA or histone modification. Some of these epigenetic modifiers have already been shown to facilitate the reprogramming process, such as BIX (Shi, Y. et al., *Cell Stem Cell*, 2:525-528 (2008)), valproic acid (Huangfu, D. et al., *Nat Biotechnol*, 26:795-797 (2008)) and 5' azacytidine (Mikkelsen, T. et al., *Nature*, 454:49-55 (2008)).

This present study demonstrates that small molecules identified through a phenotypic screen can be used to effectively compensate for the viral transduction of another critical iPSC TF, Sox2, which is not endogenously expressed in fibroblasts. Moreover, it highlights the important contribution that small molecule screens will eventually make to the discovery of new molecular targets and mechanisms involved in complicated biological processes such as reprogramming.

Results

Phenotypic Screen Leads to the Discovery of Small Molecules that Enable MEF Reprogramming when Transduced with Only Two TFs.

Figure 3:
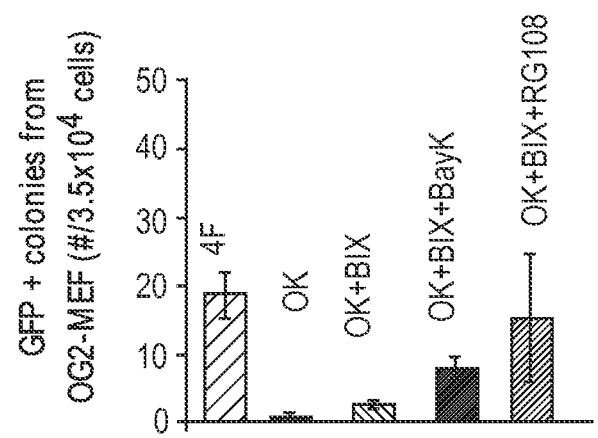
FIG. 3. Generation of OK2B iPSCs from primary OG2 MEFs. Bar graph showing the average number of GFP$^+$ colony induced from OG2-MEFs in 3 independent experiments. This graph shows data for OG2 MEF cells transduced with 4 factors (Oct4, Klf4, Sox2, and cMyc; 4F); transduced with OK (OK); transduced with OK and treated with 1 μM BIX (OK+BIX); transduced with OK and treated with 1 μM BIX+2 μM BayK (OK+BIX+BayK); transduced with OK and treated with 1 μM BIX+0.04 μM RG108 (OK+BIX+RG108), n=3, error bar represents standard deviation as calculated with Excel.

Unmodified MEFs derived from E13-14 embryos of the 129 mice were used for the initial screen. MEFs were plated on Matrigel at $3.5 \times 10^4$ cells/well of a 6-well plate and transduced with OK (retroviral vectors expressing Oct4 and Klf4) alone. Within 14-21 days, treated cells were assessed for the appearance of colonies that had the characteristic embryonic stem cell (ESC), colony morphology and were positive for the pluripotency marker alkaline phosphatase (ALP). Such OK-transduced cells generated only a few small non-compact colonies, which were weakly positive for ALP expression. These colonies initially appeared within 21 days after viral transduction and were difficult to expand. Therefore, such assay system offered a clean background for the identification of small molecules having desirable reprogramming inducing activity. Using this system, compounds from a library of around 2000 known small molecules (see Experimental Procedures below) were screened and were identified as hits when they induced the appearance of ESC colonies that were strongly positive for ALP within 14-21 days after treatment. This image-based method provided a more accurate assessment of reprogramming as compared to homogenous reporter-based assay. BIX appeared to have the strongest effect with reproducible induction of more than 1-2 compact ESC-like colonies with high ALP expression. We observed that when MEFs were treated with BIX after OK viral transduction, compact colonies with strong ALP expression could be readily detected within approximately 14-21 days. These cells were also positive for Nanog, Oct4 and SSEA-1 expression. This result, obtained with a more general cell type, which does not endogenously express any of the three essential reprogramming genes, further validates our previous observation that BIX has strong reprogramming inducing activity and inhibition of the G9a HMTase can facilitate reprogramming (Shi, Y. et al., *Cell Stem Cell*, 2:525-528 (2008)). However, the reprogramming efficiency in MEFs transduced with OK and treated with BIX was still low, about 2 colonies/$3.5 \times 10^4$ cells, in comparison to the four factor-induced reprogramming of MEFs or the OK/BIX NPC reprogramming (Shi, Y. et al., *Cell Stem Cell*, 2:525-528 (2008)). Therefore, we conducted a second screen using a similar protocol, but where BIX was added to the basal media after OK viral transduction. This provided a more permissive platform to identify new small molecules that could further improve reprogramming efficiency. More importantly, this second screen could facilitate discovery of small molecules that impact reprogramming in a more specific manner, for example by acting on signal transduction pathways rather than on histone or DNA modifying enzymes. In this second screen, we again assayed the library of around 2000 known small molecules (see Experimental Procedures), and confirmed two compounds that were able to act in a synergistic manner with BIX to improve reprogramming based on the criteria of the screen. One example is RG108, a DNA methyltransferase (DMNT) inhibitor (Brueckner, B. et al., *Cancer Res*, 65:6305-6311 (2005)), which enhanced reprogramming of OK transduced MEFs in the presence of BIX (FIG. 3). However, similarly to BIX, RG108 is known to impact the cells at a general epigenetic level, and another DNA methyltransferase inhibitor, 5-azacytidine has already been shown to enhance reprogramming (Mikkelsen, T. S. et al., *Nature*, 454:49-55 (2008)). Therefore, RG108 was not pursued further for this study. Instead, we focused our phenotypic and functional characterization on another small molecule that was identified in the second screen, BayK, an L-calcium channel agonist. This small molecule, which showed the strongest effect in the screen aside from known DNA/histone modifiers, was studied further because it has no observable reprogramming activity on OK-transduced MEFs in the absence of BIX and is not known to impact the cells directly at the epigenetic level, but rather at the cell signal transduction level. Therefore, BayK might play a more specific role in the reprogramming process. When 129 MEFs were transduced with empty retrovirus (negative control); no colonies observed. When 129 MEFs were transduced with OK without small molecules; few small flattened colonies with weak ALP expression present. ESC-like iPSC colonies were observed 14-21 days after 129 MEFs were transduced with OK and treated with BIX/BayK; these ESC-like colonies exhibited strong ALP expression. When OK-transduced MEFs were treated with BIX in combination with BayK, a significant increase in the number of ALP+ colonies that closely resemble the mESC morphology could be observed (~7 colonies) as compared to OK-transduced MEFs treated with BIX alone (~2 colonies). Further characterization of these primary iPSC colonies showed that they were positive for typical pluripotency markers such as Oct4, Sox2, Nanog, and SSEA1 as determined by immunofluorescence.

iPSCs Obtained from MEFs Transduced with OK and Treated with BIX/BayK have Pluripotency Properties Characteristic of mESCs.

To further confirm and characterize that OK transduction and BIX/BayK treatment can induce MEFs to become iPSCs, we used primary MEFs derived from OG2$^{+/-}$/ROSA26$^{+/-}$ (OG2) transgenic mice, which contain an Oct4-GFP reporter (Do, J. T. and Scholer, H. R., *Stem Cells*, 22:941-949 (2004)). Once reprogrammed, these cells could then be used to conveniently assess chimera and germline competency. Similarly to 129 MEFs, OG2 MEFs transduced with OK could generate iPSCs when treated with a combination of BayK/BIX (OK2B iPSCs) (FIG. 3). GFP$^+$ iPSC colonies could be first detected on day 14-21 after viral transduction and compound treatment. When OG2 MEFs were transduced with OK and not treated with any compounds, only a few small colonies appeared for an average of 0.5±0.7 colony per $3.5 \times 10^4$ cells. These colonies were difficult to passage and therefore were not studied any further. Treatment of OK transduced OG2 MEFs with BIX alone readily and reproducibly enabled reprogramming as compared to OK alone, with 2.5±0.7 colonies per $3.5 \times 10^4$ cells. There was a further significant improvement in the reprogramming efficiency when OG2 MEFs transduced with OK were treated with the combination of BIX (2 μM) and BayK (2 µM), where we observed 7.7±1.5 colonies per 3.5×10⁴ cells (FIG. 3). Treatment of OK-transduced OG2 MEFs with BayK alone, in the absence of BIX, did not increase reprogramming efficiency above OK-transduced MEF control (data not shown).

Figure 4:
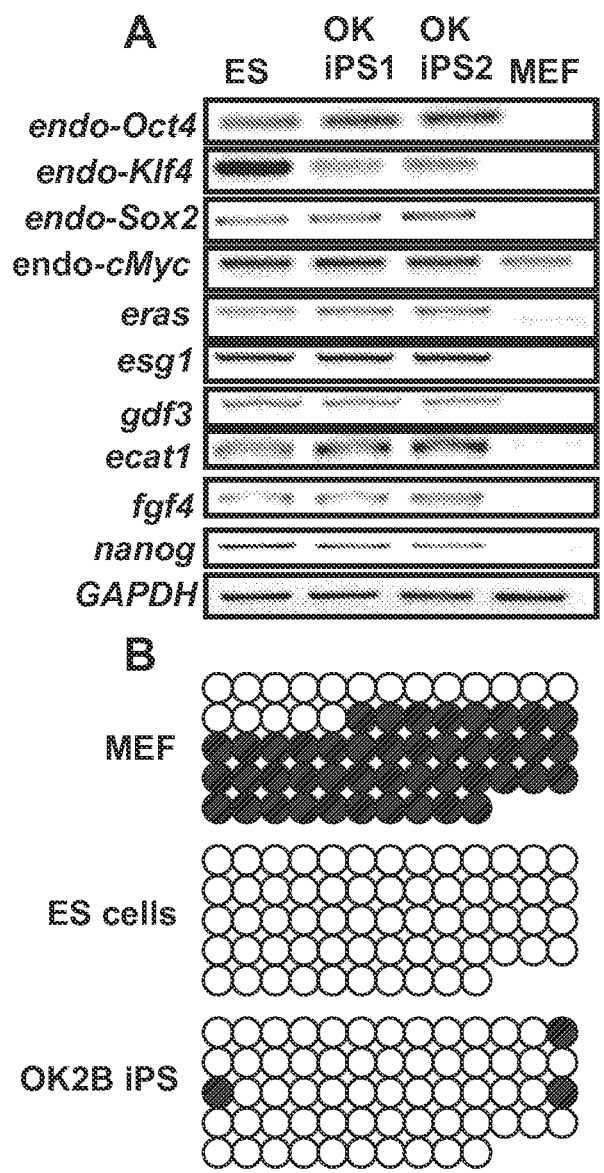
FIG. 4. OK2B iPSCs have a transcriptional profile similar to the one of mESCs. (A) RT-PCR analysis of OK2B iPSCs indicated they express genes specific to pluripotent mESCs. R1 mESCs were used as positive control while OG2 MEFs were used as negative control. GAPDH was used as loading control. (B) Bisulfite sequencing revealed that OK2B iPSCs' nanog promoter is demethylated, further suggesting a reactivation of endogenous genes specific to mESCs. Schematic depiction of the cytosine present in the region of the Nanog promoter that was amplified for this analysis. Open circle indicates demethylated cytosine, while filled/black circle indicates methylated cytosine.

OK2B colonies were picked out and serially expanded on irradiated MEF feeder cells in the conventional mESC growth conditions in the absence of small molecules for more than 20 passages. Staining and/or RT-PCR (FIG. 4A) showed that these GFP⁺ OK2B iPSCs express typical pluripotency markers, including ALP, Nanog, Sox2, Oct4, SSEA1, c-Myc, eRas, Esg1, Ecat1, and Fgf4. RT-PCR assay also demonstrated that OK2B iPSCs expressed endogenous Oct4 and Klf4 (FIG. 4A). Bisulphite genomic sequencing analyses of the Nanog promoter revealed that it is demethylated in OK2B iPSCs similarly to the mESC control (R1), while the MEFs' Nanog promoter was hypermethylated (FIG. 4B). This result further suggests a reactivation of the stem cell transcription program in these OK2B iPSCs. In addition, transcriptome analysis showed that expression profile of OK2B iPSCs is greatly similar to the one of mESCs with a Pearson correlation value of 0.96, while significantly different to MEFs' profile with a Pearson correlation value of 0.84 as exemplified in the clustering analysis.

For comparison of OK2B transcriptome with mES cells and MEF cells, transcriptome analysis was carried out. RNA was extracted from OK2B iPS cells at passage 13 using Qiagen RNAeasy Mini Kit. RNA expression data for OK2B iPSCs was generated from polyA RNA using GeneChip Mouse Genome 430 2.0 Arrays (Affymetrix). Expression data for MEF cells and mES cells were obtained from the Gene Expression Omnibus (GEO) website http://www.ncbi.nlm.nih.gov/geo/. mES cells data registry number: GSM198062. GSM198063, and GSM198064. MEF cell data registry number: GSM198070 and GSM198072. Preprocessing, normalization (GC-RMA) and hierarchical clustering were performed using dChip (http://biosun1.harvard.edu/complab/dchip/; (Distance metric: correlation (Pearson); linkage method: centroid; gene ordering: by cluster tightness). p value for OK2B iPSC versus MEF cells: 0.84; OK2B iPSC versus mES cells: 0.96. p values were obtained using a Pearson correlation test.

OK2B iPSCs Differentiate into Cells from all Three Germ Layers and Contribute to Germline Transmission.

OK2B iPSCs could efficiently form embryoid bodies (EB) in suspension, which could differentiate into endodermal cells (Albumin and Pdx1), mesodermal cells/cardiac muscle cells (CT3) and ectodermal cells/neurons (βIII-tubulin, Tuj1), derivatives of the three primary germ layers. In addition, OK2B iPSCs could efficiently incorporate into the inner cell mass of a blastocysts following aggregation with an 8-cell embryo, and lead to chimerism with germline contribution in vivo after the aggregated embryos were transplanted into pseudo-pregnant mice. Moreover, mating of one adult male progeny obtained from these blastocysts with a female CD1 wild-type mouse led to the production of LacZ⁺ progeny, three of which showed Oct4-GFP⁺ gonads further validating that these iPSCs could contribute to germline transmission. These in vitro and in vivo characterizations confirm retroviral transduction with only two genes, OK, and in conjunction with BIX/BayK treatment are sufficient to reprogram MEFs into iPSCs, which are phenotypically and functionally similar to the classic mESCs.

Discussion

Figure 5:
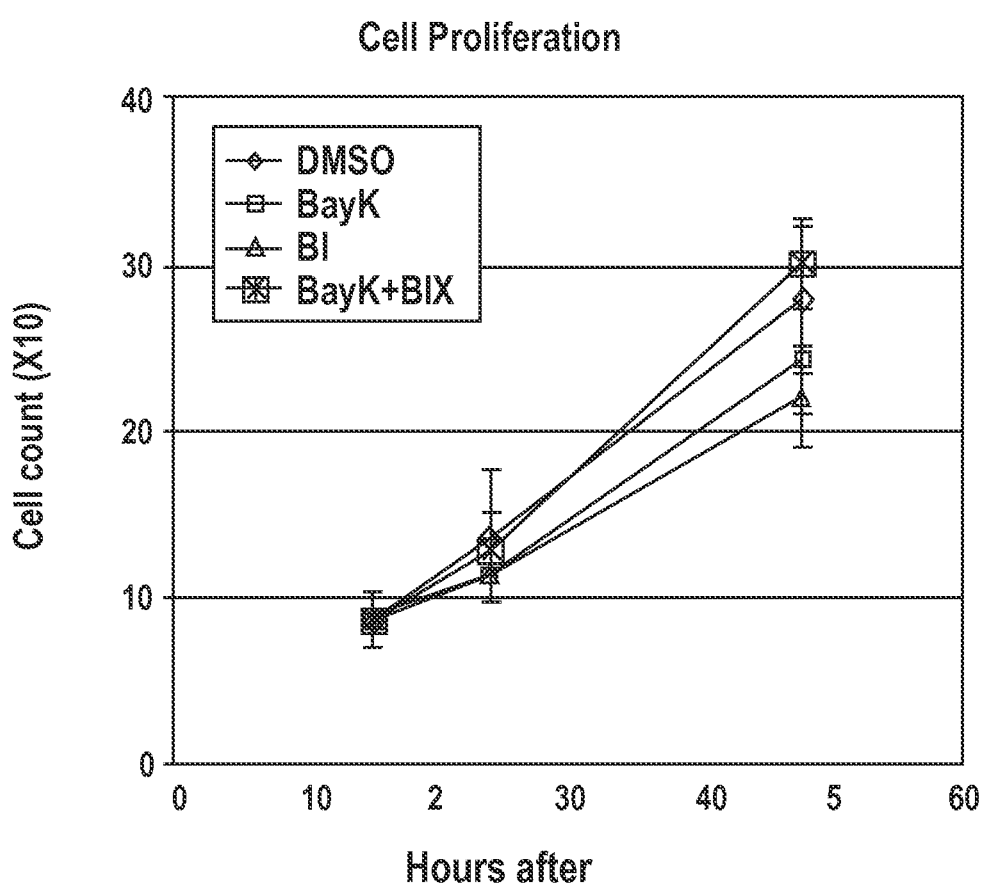
FIG. 5. Treatment with BIX, BayK or a combination of both does not increase the proliferation of mES cells. Scatter graph showing R1 mES cell number after treatment with DMSO (control), 2 μM BayK, 1 BayK, 1 μM BIX and a combination of both (BayK+BIX). n=3. The error bars represent standard deviation as calculated in Excel. No significant difference was obtained for each treatment compared to DMSO as calculated using t-test in Excel.
Figure 6:
FIG. 6. RT-PCR analysis for Sox2 expression after compound treatment. OG2$^{+/-}$/ROSA26$^{+/-}$ (OG2) MEFs were treated with DMSO (control), 1 μM BIX, 2 μM BayK, and a combination of both for 6 days. RNA was then extracted using Qiagen RNAeasy Mini Kit. Sox2 expression was assessed through semi-quantitative PCR. OK2B iPSCs p37 and R1 were used as positive control, GAPDH as loading control.

The studies presented here provide a proof-of-principle demonstration that small molecules can be identified from rationally designed phenotypic screens to functionally replace viral transduction of certain TF(s) as well as improve reprogramming efficiency in generating iPSCs from a general cell-type, like MEFs. Such a chemical approach for the generation of iPSCs, which offers more precise and temporal control of the target/process, would be advantageous over the genetic manipulation with oncogenes that may also introduce harmful hard-to-detect insertional genomic alterations. Similar strategies are being used to find additional small molecules that may ultimately allow reprogramming of lineage-restricted cells to pluripotent or multipotent state in a completely chemically defined condition. BIX was originally identified and characterized as a specific inhibitor for G9a HMTase (Kubicek, S. et al., Mol Cell, 25:473-481 (2007)). It has been shown to reduce H3K9me2 levels at G9a target genes (Feldman, N. et al., Nat Cell Biol, 8:188-194 (2006)). Interestingly, histone H3K9 methylation, mediated by G9a, and heterochromatinization represent a highly specific mechanism for epigenetic silencing of embryonic genes such as Oct4 and Rex1 (Feldman, N. et al., Nat Cell Biol, 8:188-194 (2006)). Furthermore, it was also demonstrated that knock-down of G9a can assist in fusion-based reprogramming of adult neuronal cells (Ma, D. K. et al., Stem Cells, 26:2131-2141 (2008)). It is therefore fitting that we previously observed that BIX can facilitate the generation of iPSCs from NPCs transduced with either OK or Klf4/Sox2/c-Myc (Shi, Y. et al., Cell Stem Cell, 2:525-528 (2008)), suggesting that it can compensate for the exogenous expression of Sox2 or Oct4. However, NPCs already express significant levels of Sox2, which might cause these cells to be more susceptible to reprogramming in the conditions mentioned above. This present study aimed at identifying small molecules that can enable reprogramming of MEFs, which do not express any of the TFs deemed necessary for reprogramming. It was fortuitous that we identified BIX in both the NPC and MEF screens, and further confirm this molecule has a role in enabling and improving the generation of iPSCs from somatic cells. Given BIX's characterized mechanism of action, our studies potentially identified a molecular target whose loss-of-function via pharmacological inhibition is sufficient to compensate for the gain-of-function of an essential iPSC reprogramming gene. It further mechanistically links a specific epigenetic process, inhibition of G9a-mediated H3K9me2, to iPSC generation. BIX may function to facilitate shifting of the epigenetic balance from a silenced state of pluripotency genes to an active transcription state. Obviously, combination of BIX with other chromatin-modifying small molecules, which have different targets and mechanisms of action, such as RG108 could be exploited for better reprogramming. On the other hand, our observation that BayK, with a characterized activity as a specific L-type calcium channel agonist (Schramm, M. et al., Nature, 303:535-537 (1983)), improves reprogramming efficiency is intriguing. L-type calcium channels are known to mediate intracellular processes in different tissues such as blood pressure regulation, smooth muscle contractility, insulin secretion, cardiac development, etc (Tosti, E., Reprod Biol Endocrinol, 4:26 (2006)). Furthermore, activation of L-type calcium channels by different agonists, including BayK, has been shown to induce intracellular signaling through CREB activation, sarcoplasmic reticulum $Ca^{2+}$ release, and change in cAMP activity. More importantly, some reports suggest that calcium might play a role in the control of mES cell proliferation (Heo, J. S. et al., Am J Physiol Cell Physiol, 290:C123-133 (2006)). However, in our hands, treatment of mES cell with 2 µM BayK alone or in combination with 1 µM BIX does not lead to a change in proliferation (FIG. 5). Furthermore, treatment of OG2 MEF with 2 µM BayK alone or in combination with 1 µM BIX does not induce SOX2 expression (FIG. 6). Needless to say, more work needs to be performed to dissect the precise mechanism by which BayK impacts the reprogramming process. However, it is interesting to find that a small molecule with activity in signaling pathways that have not been previously linked to reprogramming can significantly enhance its efficiency. So far, it is the first small molecule of its type, aside from Wnt3 protein (Marson, A. et al., *Cell Stem Cell*, 3:132-135 (2008)), to show an effect on reprogramming without acting directly on chromatin modifiers. As, up to date, most of the other small molecules found to impact reprogramming appear to directly modify the epigenetic status of the cell: i.e., BIX (Shi, Y. et al., *Cell Stem Cell*, 2:525-528 (2008)), valproic acid (Huangfu, D. et al., *Nat Biotechnol*, 26:795-797 (2008)) and 5' azacytidine (Mikkelsen, T. S. et al., *Nature*, 454:49-55 (2008)). Importantly, BayK seems to have several important characteristics that would be ultimately desirable for a molecule to be therapeutically relevant for in vivo reprogramming and/or regeneration. The fact that it does not act/reprogram on its own, but needs the presence of BIX to exert its effects suggests that cells that are already undergoing a form of reprogramming, perhaps caused by injury, might be more susceptible to its effect. This might allow us to ultimately reprogram the target cell in a more specific manner, without impacting healthy cells systemically, as direct epigenetic modifiers might.

In summary, we have identified defined small molecule conditions, i.e., BIX, and combinations of BIX/BayK, or BIX/RG108, which can enable and improve reprogramming of fibroblasts into iPSCs in conjunction with the transduction of only two TFs: Oct4 and Klf4. This study further confirms the usefulness of a phenotypic screening approach in identifying small molecules that can effectively compensate for the viral transduction of an essential iPSC TF, such as Sox2 in this study or Oct4 as previously reported (Shi, Y. et al., *Cell Stem Cell*, 2:525-528 (2008)). Ultimately, phenotypic small molecule screens may lead to the identification of small molecule that will become powerful tools in providing us with new insights into the reprogramming process, and may ultimately be useful to in vivo stem cell biology and therapy.

Experimental Procedures

MEFs Derivation

129S2/SvPasCrlf or ROSA26$^{+/-}$/OG2$^{+/-}$ MEFs were derived according to the protocol reported on WiCell Research Institute website: "Introduction to human embryonic stem cell culture methods." Animal experiments were performed according to the Animal Protection Guidelines of the Max Planck Institute for Biomolecular Research, Germany.

Retrovirus Transduction and Compounds pMX-based retroviral vectors for mouse Oct4, Klf4, c-Myc and Sox2 were obtained from Addgene (Cambridge, Mass.). The viral production and transduction process was performed as described (Takahashi, K. et al., *Cell*, 131:861-872 (2007)). The synthesis and full characterization of compound BIX-01294 was as previously described (Kubicek, S. et al., *Mol Cell*, 25:473-481 (2007)) and Bayk8644 was purchased from EMD/Calbiochem Biochemical (San Diego, Calif.).

Screen for iPSC Generation from MEFs

For the primary and secondary screens, a collection of known compounds was used. This collection was composed of roughly 2000 known bioactive molecules that are commercially available, including FDA-approved drugs, known inhibitors and activators of characterized enzymes (including LOPAC collection from Sigma-Aldrich (St. Louis, Mo.), Known Bioactive Library from BIOMOL (Plymouth Meeting, Pa.) and non-overlapping known compounds from EMD Calbiochem (San Diego, Calif.)).

Primary 129S2/SvPasCrlf (primary screen) or ROSA26$^{+/-}$/OG2$^{+/-}$ (secondary screen) MEFs were plated onto Matrigel (1:50; BD Biosciences, Bedford, Mass.) coated dishes at a density of $3.5 \times 10^4$ cells per well of a 6-well plate. Twenty-four hours later, these cells were transduced overnight with defined retroviruses at 37° C., 5% $CO_2$. Twelve to fourteen hours later, the media on the transduced cells was changed to mESC medium [Knockout DMEM, 10% ES-qualified FBS, 10% Knockout serum replacement, 1% Glutamax, 1% Non-essential amino acids, penicillin/streptomycin, 0.1 mM β-mercaptoethanol, 1% EmbryoMax ESC Qualified Nucleosides (Millipore, Temecula, Calif.), and $10^3$ U/ml LIF (Millipore)] (all products were from Invitrogen, Carlsbad, Calif., except where mentioned). On that same day, individual small molecules from our known drug collection were added to the cells at a range between 0.5 and 2 µM. Compound treatment was continued for 10-14 days; the cells were fixed and stained on day 14-21 using a standard ALP detection kit (Millipore). For the second screen, 1 µM BIX was added to the mESC medium 1 day after transduction. Five days later, in addition to 1 µM BIX, individual small molecule from the known drug collection was added to each well, at a range between 0.5 and 2 µM. Mouse ESC media with defined small molecules was refreshed every three days until colonies with a similar morphology to mESCs were observed, which was usually between 14-21 days after transduction. In addition to the confirmed compounds as indicated in the text, primary hits from the second synergist screen that were not further followed up also include PD173074, reversine, 5' azacytidine, pluripotin, and dexamethasone. Further characterization studies and repeats were carried either on primary 129S2/SvPasCrlf or ROSA26$^{+/-}$/OG2$^{+/-}$ MEFs. When ROSA26$^{+/-}$/OG2$^{+/-}$ MEFs were used, the iPSC colonies could also be identified through GFP expression, as a marker of Oct4 expression. Once iPSC colonies were identified, they were picked for expansion on MEF feeder cells in mESC medium. Some colonies were expanded in the presence of the MEK inhibitor, PD0325901 at concentration of 0.5-2 µM to further confirm their pluripotentiality.

Immunocytochemistry and Immunofluorescence Assay

ALP staining was performed according to manufacturer's instruction using the Alkaline Phosphatase Detection Kit (Millipore). For immunofluorescence assay, cells were fixed in 4% paraformaldehyde 15 minutes at room temperature (RT) and washed with PBS. They were then incubated in blocking buffer (BB) [0.3% Triton X-100 (Sigma-Aldrich), 10% normal donkey serum (Jackson ImmunoResearch Laboratories Inc) in PBS (Invitrogen)] 30 min at RT. They were then incubated with primary antibody overnight at 4° C. in BB. Afterward, cells were washed with PBS and incubated with secondary antibody in BB for 45-60 min at RT. Primary antibodies were; mouse anti-Oct4 (1:200) (Santa Cruz Biotechnology, Inc., Santa Cruz, Calif.), mouse anti-SSEA1 (1:200) (Santa Cruz Biotechnology Inc.), rabbit anti-Nanog (1:500) (Abcam Inc., Cambridge, Mass.), mouse anti-Sox2 (1:200) (Millipore), rabbit anti-Pdx1 (1:200) (a kind gift from Dr. C. Wright), mouse anti-βIII-Tubulin (Tuj1) (1:500) (Covance Research Products Inc., Denver, Pa.), mouse anti-cardiac troponin T (CT3) (1:200) (Developmental Studies Hybridoma Bank at the University of Iowa, Iowa City, Iowa), rabbit anti-albumin (DAKO). Secondary antibodies were Alexa Fluor555 donkey anti-mouse or rabbit IgG (1:500) (Invitrogen). Nuclei were detected by DAPI (Sigma-Aldrich) staining. Images were captured using a Nikon Eclipse TE2000-U/X-cite 120 EXFO microscope with a photometric CoolSnap HQ2 camera.

RT-PCR Assay

RNA was extracted from iPSCs and control cell lines using the RNeasy Plus Mini Kit in combination with QIAshredder. The RNA was converted to cDNA using iScript™cDNA Synthesis Kit (BioRad, Hercules, Calif.). Amplification of specific genes was done using primers previously published (Takahashi, K. et al., *Cell*, 131:861-872 (2007); Takahashi, K. and Yamanaka, S., *Cell*, 126:663-676 (2006)) and Platinum PCR SuperMix (Invitrogen) on a Mastercycler ep gradient PCR machine (Eppendorf).

Methylation Assay

DNA from R1, OG2 MEFs and OK iPSCs (passage 10) cells was isolated using the Non Organic DNA Isolation Kit (Millipore). The DNA was then treated for bisulfite sequencing with the EZ DNA Methylation-Gold Kit™ (Zymo Research Corp., Orange, Calif.). The treated DNA was then used to amplify sequences of interest. Primers used for promoter fragment amplification were as previously published (Blelloch, R. et al., *Stem Cells*, 24:2007-2013 (2006)). The resulting fragments were cloned using the TOPO TA cloning Kit for sequencing (Invitrogen) and sequencing was done.

Aggregation of iPSCs with Zona-Free Embryos iPSCs were aggregated with denuded post-compacted eight-cell stage embryos to obtain aggregate chimeras. Eight-cell embryos (B6C3F1) were flushed from females at 2.5 dpc and cultured in microdrops of KSOM medium (10% FCS) under mineral oil. Clumps of iPSCs (10-20 cells) after short treatment of trypsin were chosen and transferred into microdrops containing zona-free eight-cell embryos. Eight-cell embryos aggregated with iPSCs were cultured overnight at 37° C., 5% $CO_2$. Aggregated blastocysts that developed from eight-cell stage were transferred into one uterine horn of a 2.5 dpc pseudopregnant recipient. One adult male chimaera was mated with a female CD1 wild-type mouse. X-gal staining showed that six F1 embryos obtained from this natural mating of chimeric mouse and wild-type mouse were generated by germline transmission.

Statistical Analysis

Bar graphs and statistical analyses were performed using a standard t-test on the Excel.

Microarray Analysis

OK2B iPSCs were grown in complete mES cell media on gelatin (Millipore, Temecula, Calif.) for 2 days [Knockout DMEM, 10% ES-qualified FBS, 10% Knockout serum replacement, 1% Glutamax, 1% Non-essential amino acids, penicillin/streptomycin, 0.1 mM β-mercaptoethanol, 1% EmbryoMax ESC Qualified Nucleosides (Millipore), and $10^3$ U/ml LIF (Millipore)] (all products were from Invitrogen, Carlsbad, Calif., except where mentioned). RNA from duplicate wells was then isolated using RNAeasy Mini Kit (Qiagen, Valencia, Calif.). Total RNA samples were amplified and labeled using the MessageAmp II-Biotin Enhanced Kit (Ambion, Austin, Tex.). The amplified labeled samples were then hybridized to Mouse Genome 430 2.0 Arrays (Affymetrix) and analysis was performed using hierarchical clustering (Pearson, log-transformed, row-centered values) using GenePattern (world wide web at: broad.mit.edu/cancer/software/).

Proliferation Assay mES R1 cells were plated onto gelatin-coated 6-well plates at a density of $2 \times 10^5$ cells/well in complete mES cell media. Upon cell attachment, app. 12 hours, the cells were treated either with DMSO, 1 µM BIX, 2 µM BayK, and a combination of both, in triplicate. At 15, 24 and 48 hours, the cells were detached using trypsin, and counted using a hemocytometer. Trypan blue (Sigma-Aldrich, St. Louis, Mo.) was used for dead cell exclusion.

Assessment of SOX2 Expression after Compound Treatment $OG2^{+/-}$/$ROSA26^{+/-}$ MEFs were plated onto 6-well plate at a density of $3.4 \times 10^4$ cells per well. On the following day, the cells were treated with DMSO, 1 µM BIX, 2 µM BayK, and a combination of both, in triplicate, for 6 days. The media was refreshed at day 3. RNA from each well was then isolated using the RNAeasy Mini Kit (Quiagen). Reverse transcription of the RNA was performed using the iScript™cDNA Synthesis Kit (BioRad, Hercules, Calif.). Amplification of endogenous Sox2 was done using primers previously published (Takahashi, K., Okita, K., Nakagawa, M., and Yamanaka, S. (2007). Induction of pluripotent stem cells from fibroblast cultures. Nat Protoc 2, 3081-3089; Takahashi, K., and Yamanaka, S. (2006). Induction of pluripotent stem cells from mouse embryonic and adult fibroblast cultures by defined factors. Cell 126, 663-676) with Platinum PCR SuperMix (Invitrogen) on a Mastercycler® ep gradient PCR machine (Eppendorf).

Example 3

This example demonstrates that incubation of mammalian cells with transcription factor proteins is sufficient to induce pluripotency.

Gene Construction:

In order to obtain the high level protein expression in *E. coli*, all four human TF gene codon region were optimized first (G A Gutman and G W Hatfield (1989). PNAS. vol. 86. pp:3699-3703), and full-length synthesized using DNA oligo based/PCR gene assembling technology (Danilo R Casimiro, Peter E Wright & H Jane Dyson. (1997). Structure. Vol. 5. pp: 1407-1412.). Poly-arginine tag: ESGGGGSPGRRRRRRRRRRR (SEQ ID NO:2) was added to each protein C-terminal in design (Gump J M, Dowdy S F. (2007) Trends Mol Med. Oct; 13(10):443-8). The final DNA fragment was flanked with NdeI and XhoI site, and inserted into pET41 expression vector NdeI-XhoI sites for protein expression. Each plasmid were verified with DNA sequence, then transformed into BL21start competent cells for recombinant protein production using auto-induction medium overnight (Studier F W, (2005) Protein Expr Purif. 41(1). Pp: 207-234.).

Protein Preparation

*Escherichia coli* BL21(DE3) cells were transformed with pET-Oct4-PTD ("PTD" refers to protein transduction domain), pET-Sox2-PTD, pET-Klf4-PTD, and pET-c-Myc-PTD separately, and the protein expression was done using the auto-induction method (Studier F. W., Protein Expression and Purification, 41 (2005) 207-234.). Inclusion bodies were solubilized and the proteins were refolded as described (LaFevre B M, Wu S. & Lin X. Molecular Cancer Therapeutics 7, 1420-1429, Jun. 1, 2008. doi: 10.1158/1535-7163; Medynski D., Tuan M., Liu, W., Wu, S. & Lin, X. Protein Expression and Purification Vol. 52, 395-402, April 2007; Hou W., Medynski D., Wu, S., Lin, X. & Li, L Y. Clinical Cancer Research Vol. 11, 5595-5602, Aug. 1, 2005).

Briefly, E. coli containing an expression plasmid was inoculated into 1.0 L liter of Luria-Bertani Broth containing kanamycin, induced with 500 umol/L IPTG at A600 nm=0.6, and agitated for 3 hours at 37 C. The cells were collected by centrifugation, and the pellet subjected to freeze-and thaw cycles. The inclusion bodies released were washed extensive with a buffer containing 20 mmol/L tris, 100 mmol/L NaCl, 1% TritonX-100 (pH8.0) and dissolved in a buffer containing 8 mol/L urea, 0.1 mol/L Tris, 1 mmol/L glycine, 1 mmol/L EDTA, 10 mmol/L b-mercaptoethanol, 10 mmol/L DTT, 1 mmol/L reduced glutathione, 0.1 mmol/L oxidized glutathione (pH 10) with a A280 nm=2.0. The solubilized inclusion bodies were refolded with a rapid dilution method as described (Lin X L, Lin Y Z, Tang J., Methods Enzymol 1994, 241, 195-224; Lin X, Koelsh G., Wu. S, Downs D, Dashti A. Tang J. Proc Natl Acad Sci USA. 2000; 97, 1556-1560; Kim Y T. Downs D. Wu S, et al. Eur J Biochem 2002, 269: 5669-77; Michelle LaFevre-Bernt, Shili Wu, and Xinli Lin. (2008). Molecular Cancer Therapeutics. 7: pp: 1420-1429). The refolded protein was concentrated by N2-ultrafiltration and purified by size exclusion chromatography using Sephacryl S 300. The endotoxin concentration in each of protein preparation was less than 100 EU/mg. Most refold protein samples have solubility at least >1.5 mg/ml.

Refolded proteins were concentrated using tangential flow filtration, purified using size exclusion chromatography with a Superdex-200 column (XK26×850-mm, GE, Piscataway, N.J.), and confirmed using SDS-PAGE.

Mouse fibroblasts were grown in mESC medium supplemented with 8 µg/ml of either Oct4/Sox2/Klf4 or Oct4/Sox2/Klf4/Myc (all proteins comprising poly-Arg as described above) for 6-8 hours, washed, and incubated for 2-3 days in mESC media without the above-listed transcription factors. This (4-12 hours with, 1-3 days without) was repeated a number (1, 2, 3, 4, or more) of times and then the cells were cultures in mESC for two weeks. At the end of this period, the cultures were determined to contain pluripotent cells by colony morphology and marker expression (data not shown). Notably, it was found that constant incubation of the cells with the transcription factors (i.e., without the 1-3 day period without the proteins)) was toxic to the cells. While it was not necessary, the cells were sometimes incubated with MEK inhibitor (PD0325901) and/or GSK inhibitor (CHIR99021) and/or TGFbeta inhibitor (SB431542) and the presence of these agents improved efficiency and speed of development of pluripotent cells.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. An in vitro method of producing an induced pluripotent stem cell from a mammalian non-pluripotent cell, the method comprising:
    (a) contacting the mammalian non-pluripotent cell with a MEK inhibitor; and
    (b) introducing into the mammalian non-pluripotent cell, one or more expression cassettes comprising nucleic acids encoding an Oct4 polypeptide and a Klf4 polypeptide, thereby producing an induced pluripotent stem cell;
    wherein the introducing step does not comprise introducing a Myc polypeptide or introducing an expression cassette comprising a nucleic acid encoding a Myc polypeptide.

2. The method of claim 1, wherein the contacting step further comprises contacting the mammalian non-pluripotent cell with a TGFβ receptor/ALK5 inhibitor.

3. The method of claim 1, wherein the contacting step further comprises contacting the mammalian non-pluripotent cell with a TGFβ receptor/ALK5 inhibitor and a GSK3 inhibitor.

4. The method of claim 2 or 3, wherein the TGFβ receptor/ALK5 inhibitor is selected from the group consisting of SB431542 and A-83-01.

5. The method of claim 3, wherein the TGFβ receptor/ALK5 inhibitor is selected from the group consisting of SB431542 and A-83-01; and the GSK3 inhibitor comprises CHIR99021.

6. A composition comprising a mammalian non-pluripotent cell; one or more expression cassettes comprising nucleic acids encoding a Klf4 polypeptide, an Oct4 polypeptide, and/or a Sox2 polypeptide; and at least one of a TGFβ receptor/ALK5 inhibitor, a GSK3 inhibitor, and a MEK inhibitor, wherein the one or more expression cassettes does not encode a Myc polypeptide.

7. The composition of claim 6, comprising an expression cassette comprising a nucleic acid encoding the Oct4 polypeptide.

8. The method of claim 1, further comprising contacting the mammalian non-pluripotent cell with at least one of: an agent that inhibits H3K9 methylation or promotes H3K9 dernethylation; an L-type Ca channel agonist; an activator of the cAMP pathway; DNA methyltransferase (DNMT) inhibitor; a nuclear receptor ligand; a GSK3 inhibitor; a TGFβ receptor/ALK5 inhibitor; a HDAC inhibitor; and an Erk inhibitor.

9. The method of claim 1, wherein the MEK inhibitor comprises PD0325901.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (11)..(11)
<223> OTHER INFORMATION: AMIDATION

<400> SEQUENCE: 1

Lys Glu Ala Pro Pro Ala Pro Pro Gln Ser Pro
1               5                   10

<210> SEQ ID NO 2
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 2

Glu Ser Gly Gly Gly Gly Ser Pro Gly Arg Arg Arg Arg Arg Arg Arg
1               5                   10                  15

Arg Arg Arg Arg
            20
```